(12) United States Patent
Lewis et al.

(10) Patent No.: US 9,913,608 B2
(45) Date of Patent: *Mar. 13, 2018

(54) INCONTINENCE MONITORING AND ASSESSMENT

(71) Applicant: Fred Bergman Healthcare Pty. Ltd., North Sydney (AU)

(72) Inventors: Philippa Mary Lewis, Mosman (AU); Karen Maree Carey, Lower Templestowe (AU); Alan Michael Cottenden, Bedfordshire (GB); David Albert Barda, Rose Bay (AU); Peter Curran, Oatley (AU); Don Black, Albert Park (AU)

(73) Assignee: Fred Bergman Healthcare Pty. Ltd., North Sydney (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/013,050

(22) Filed: Feb. 2, 2016

(65) Prior Publication Data

US 2016/0220164 A1 Aug. 4, 2016

Related U.S. Application Data

(63) Continuation of application No. 13/508,071, filed as application No. PCT/AU2010/001471 on Nov. 5, 2010, now Pat. No. 9,283,123.

(Continued)

(51) Int. Cl.
*G08B 23/00* (2006.01)
*A61B 5/20* (2006.01)
(Continued)

(52) U.S. Cl.
CPC .............. *A61B 5/202* (2013.01); *A61B 5/002* (2013.01); *A61B 5/207* (2013.01); *A61B 5/208* (2013.01);
(Continued)

(58) Field of Classification Search
CPC ......... A61F 13/42; A61B 5/202; A61B 5/207; A61B 5/208; A61B 5/038; A61B 5/14532; A61B 5/1473; A61B 5/055; A61B 5/1495
(Continued)

(56) References Cited

U.S. PATENT DOCUMENTS 5,289,372 A * 2/1994 Guthrie ................. G06F 11/006
340/5.92
6,583,722 B2 * 6/2003 Jeutter .................... A61F 13/42
340/572.2
(Continued)

*Primary Examiner* — Hoi Lau
(74) *Attorney, Agent, or Firm* — Hansen IP Law PLLC

(57) ABSTRACT

A system for monitoring incontinence in one or more subjects comprises display means; input means operable by a user; one or more transmitters, each transmitter being associated with one or more subjects being monitored; the one or more transmitters being configured to transmit signals containing continence-related data for the one or more subjects, wherein the continence-related data has been obtained over time from a continence sensor associated with an absorbent article worn by each respective subject; a receiver unit configured to receive signals from the one or more transmitters; and processing means in communication with at least the receiver unit, the processing means including a display processor configured to process the received signals and communicate display information to the display means for display of a visual representation of continence-related information derived from continence sensors in the absorbent articles worn by the one or more subjects being monitored. The system may include a volume estimator and means for communicating to a carer a 'risk of wetness leakage' based on e.g. an estimated volume of wetness and e.g. a pad type. Pad type may be communicated to the system automatically by way of a pad type indicator associated with the pad and/or pad/sensor combination.

21 Claims, 11 Drawing Sheets

Related U.S. Application Data

(60) Provisional application No. 61/351,427, filed on Jun. 4, 2010.

(51) Int. Cl.
    *A61F 13/42*        (2006.01)
    *A61B 5/00*         (2006.01)
    A61B 5/1473      (2006.01)
    A61B 5/1495      (2006.01)

(52) U.S. Cl.
    CPC ............ *A61F 13/42* (2013.01); *A61B 5/1473* (2013.01); *A61B 5/1495* (2013.01); *A61F 2013/424* (2013.01)

(58) Field of Classification Search
    USPC .... 340/573.5, 573.1, 604, 602, 539.11, 10.1, 340/540, 501, 635; 604/361, 362
    See application file for complete search history.

(56) References Cited

U.S. PATENT DOCUMENTS

| | | | | |
|---|---|---|---|---|
| 6,916,968 B2 * | 7/2005 | Shapira | ............... | A61F 13/42 340/571 |
| 7,049,969 B2 * | 5/2006 | Tamai | ............... | A61F 13/42 340/572.4 |
| 7,241,933 B2 * | 7/2007 | Shapira | ............... | A61F 13/42 340/573.6 |
| 7,250,547 B1 * | 7/2007 | Hofmeister | ............... | A61F 13/42 340/573.5 |
| 7,789,869 B2 * | 9/2010 | Berland | ............... | A61F 13/42 340/571 |
| 7,855,653 B2 * | 12/2010 | Rondoni | ............... | A61F 13/42 340/539.12 |
| 7,977,529 B2 * | 7/2011 | Bergman | ............... | A61F 13/42 604/361 |
| 8,057,454 B2 * | 11/2011 | Long | ............... | A61F 13/42 604/361 |
| 8,421,636 B2 * | 4/2013 | Collette | ............... | A61F 13/42 340/539.12 |
| 8,471,715 B2 * | 6/2013 | Solazzo | ............... | A61F 13/42 200/61.04 |
| 2002/0070864 A1 * | 6/2002 | Jeutter | ............... | A61F 13/42 340/573.1 |
| 2002/0070868 A1 * | 6/2002 | Jeutter | ............... | A61F 13/42 340/604 |
| 2003/0011479 A1 * | 1/2003 | Bluteau | ............... | A61F 13/42 340/573.5 |
| 2003/0137425 A1 * | 7/2003 | Gabriel | ............... | A61F 13/42 340/573.5 |
| 2004/0100376 A1 * | 5/2004 | Lye | ............... | A61B 5/411 340/539.12 |
| 2004/0207530 A1 * | 10/2004 | Nielsen | ............... | A61F 13/42 340/604 |
| 2004/0254554 A1 * | 12/2004 | Mavinkurve | ............... | A61F 13/4756 604/380 |
| 2006/0290517 A1 * | 12/2006 | Cohen | ............... | A61B 5/038 340/573.1 |
| 2007/0252713 A1 * | 11/2007 | Rondoni | ............... | A61B 5/202 340/573.5 |
| 2007/0252714 A1 * | 11/2007 | Rondoni | ............... | A61B 5/0002 340/573.5 |
| 2008/0000779 A1 * | 1/2008 | Wang | ............... | A61B 5/14532 205/775 |
| 2008/0074274 A1 * | 3/2008 | Hu | ............... | A61F 13/42 340/573.5 |
| 2008/0122638 A1 * | 5/2008 | Gabriel | ............... | A61F 13/42 340/604 |
| 2008/0122639 A1 * | 5/2008 | Gabriel | ............... | A61F 13/42 340/604 |
| 2008/0129519 A1 * | 6/2008 | Gabriel | ............... | A61F 13/42 340/573.5 |
| 2008/0266117 A1 * | 10/2008 | Song | ............... | A61F 13/42 340/573.5 |
| 2008/0278336 A1 * | 11/2008 | Ortega | ............... | A61B 5/1113 340/573.5 |
| 2009/0149825 A1 * | 6/2009 | Berland | ............... | A61F 13/42 604/361 |
| 2009/0161907 A1 * | 6/2009 | Healey | ............... | B65F 1/14 382/100 |
| 2009/0174559 A1 * | 7/2009 | Rondoni | ............... | A61B 5/0002 340/573.5 |
| 2009/0322543 A1 * | 12/2009 | Crnkovich | ............... | A61F 13/42 340/604 |
| 2010/0271212 A1 * | 10/2010 | Page | ............... | A61B 5/4216 340/573.1 |
| 2011/0095884 A1 * | 4/2011 | Xu | ............... | A61F 13/42 340/539.11 |
| 2012/0268278 A1 * | 10/2012 | Lewis | ............... | A61F 13/42 340/573.5 |

\* cited by examiner

INCONTINENCE MONITORING AND ASSESSMENT

CROSS-REFERENCE TO RELATED APPLICATIONS

This application is a continuation of U.S. patent application Ser. No. 13/508,071, filed Jul. 13, 2012, which is a U.S. national stage entry of PCT/AU2010/001471, filed Nov. 5, 2010, which claims the benefit of U.S. Provisional Application No. 61/351,427, filed Jun. 4, 2010. The entirety of each of the foregoing applications is hereby incorporated by reference.

FIELD OF THE INVENTION

The present invention relates to systems for use in monitoring subjects suffering from incontinence. It relates particularly, but not exclusively, to a system, method and devices for monitoring incontinence by sensing wetness in an absorbent article worn by an incontinence sufferer using a sensor associated with the article and processing the sensor signals for visual display of continence-related information and analysis.

BACKGROUND TO THE INVENTION

Incontinence is a condition in which there is uncontrolled release of natural discharges or evacuations from the bladder and/or bowel. Urinary incontinence refers to loss of bladder control resulting in involuntary or uncontrolled urination. While some forms of incontinence, particularly urinary/bladder incontinence are relatively widespread, the condition typically affects the elderly and the infirm and is more prevalent among women.

For incontinence sufferers who are unable to anticipate the need for toileting or are unable to attend to toileting without assistance, the condition when left unchecked can cause discomfort and embarrassment. In some severe cases, unchecked wetness can lead to infection arising from bacteria in bodily exudate.

Although relatively widespread, incontinence is a condition requiring treatment with sensitivity. In the past, to comply with regulations and protocols and to ensure that incontinence sufferers in care institutions such as hospitals, nursing homes, aged care facilities and geriatric institutions are appropriately cared for, it has been necessary for staff to manually check these patients on a regular basis. Apart from the unpleasantness involved with manual checks, such a regimen also places a strain on staff resources. Manually checking for wetness can also cause interruption to a patient's rest and sleep.

Incontinence indicators and detection systems exist. However, they have done little to improve the current situation in which carers must manually and repeatedly check patients for wetness. Existing incontinence detection systems are generally unable to distinguish a urinary incontinence event from a faecal incontinence event. Existing systems are also deficient in that they typically alert a carer when any wetness is detected, with no indication of the degree of wetness present. This can cause more time wasted than saved as very small volumes e.g. of urine or perspiration may trigger an alert even though the patient does not actually require attention from a carer. This can also be disturbing for the patient.

Some incontinence monitoring systems involve complicated circuitry and are expensive and difficult to manufacture. Since most diapers and pads are disposable both for efficiency of use and hygiene reasons, complicated sensor systems do not lend themselves to widespread uptake and ongoing use. Other systems are clumsy to use and the sensors can interfere with the absorbent capacity of the diaper or pad with which they are used. Others again are generally incompatible with current care practices and actually create additional work, significant complications or changes in care practices undermining any benefits they may offer and making them less susceptible to widespread uptake and ongoing use.

The present invention aims to improve upon these systems, or at least provide viable alternative for monitoring and managing incontinence.

The discussion of the background to the invention included herein including reference to documents, acts, materials, devices, articles and the like is intended to explain the context of the present invention. This is not to be taken as an admission or a suggestion that any of the material referred to was published, known or part of the common general knowledge in the patent area as at the priority date of any of the claims.

SUMMARY OF THE INVENTION

Viewed from one aspect, the present invention provides a system for monitoring incontinence in one or more subjects, the system comprising: a display means; input means operable by a user; one or more transmitters, each unit being associated with one or more subjects being monitored; the one or more transmitters being configured to transmit signals containing continence-related data for the one or more subjects, wherein the continence-related data has been obtained over time from a continence sensor associated with an absorbent article worn by each respective subject; a receiver unit configured to receive signals from the one or more transmitters; and processing means in communication with at least the receiver unit, the processing means including a display processor configured to process the received signals and communicate display information to the display means for display of a visual representation of continence-related information derived from continence sensors in the absorbent articles worn by the one or more subjects being monitored.

The processing means may be provided in a single processing device or may be provided by a number of discrete or connected processing units or processing elements which each may perform different processing functions that contribute to the overall functionality of the system. Thus, as will become apparent throughout this description, various functions of the processing means may be provided by various elements of the system including a processing element which may, in some embodiments, be associated with continence sensors per se, and/or a processing element contained within transmitters or receivers of the system, or a processing element provided as part of a "central monitor" in a particular site employing the system, or in communication with one or more of the foregoing by wired or wireless connection with other processing elements through wide area networks (WANs), local area networks (LANs), the Internet and other networks as may be known in the art.

Preferably, the processing means includes a volume estimator configured to use the continence-related data and a mathematical model to estimate a volume of wetness in the absorbent article. The volume estimator may estimate discrete volumes of individual wetness events detected in the absorbent articles being monitored. The estimates of discrete volumes may be quantified as an actual volume in milliliters. Alternatively, the volume estimate may be categorised so that individual wetness events are identifiable as small, medium or large volume amounts. Alternatively/additionally, the volume estimator may provide for identification of wetness in various events as being urinary, faecal, or a mix of faeces and urine.

Alternatively/additionally, the volume estimator may estimate cumulative wetness volume in an absorbent article. The cumulative volume may be quantified in milliliters or alternatively/additionally, the cumulative wetness volume estimate may provide for categorisation such as damp, wet and soaked. Alternatively/additionally, the cumulative wetness volume estimate may provide for an indication to be communicated to a user of when the cumulative volume of wetness in the pad is below a minimum threshold amount, between a minimum and a maximum threshold amount or above a maximum threshold amount.

Transmitters may be low power or high power devices or a combination of these, depending on the architectural model over which the system is deployed. High power transmitters may transmit data directly (e.g. over a wireless LAN or WAN) to a remotely located processing means, via the receiver. Alternatively, low power transmitters may transmit to a further transmission device in near proximity, wherein the further transmission device is a higher power device and/or a repeater (or series of repeaters) for transmitting signals to the processing means via the repeater.

Preferably, the processing means is configured to receive automatically a pad type indicator for an absorbent article worn by a subject and, based on the pad type indicator and continence-related data, calculate a risk of wetness leakage from the absorbent article. The risk of wetness leakage calculation is preferably dynamic and based on continence-related data obtained from the subject over time, preferably in real time. In a preferred embodiment, the display means provides a risk of wetness leakage indicator for an absorbent article worn by a subject being monitored.

The pad type indicator may be determined by reference to a characteristic of an identifier circuit on the absorbent article such as e.g. resistance, impedance, capacitance, inductance, a resonant frequency or a carrier frequency associated with the identifier circuit or a potential difference of current value measurable from the identifier circuit. In one embodiment, the identifier circuit exists in parallel with a sensing circuit on the absorbent article. In one embodiment, the pad type is determined by reference to a resistance value in the identifier circuit, wherein a designated pad type is associated with a designated resistance value. Pad type may relate e.g. to volume capacity of the absorbent article or to a model number of an absorbent article used with the system. In one embodiment, the processing means refers to a look up table to ascertain the pad type from the resistance value (or other characteristic) on the identifier circuit. This is particularly useful when pads are manufactured with the sensor integral to the manufacturing process. However sensors may also be applied to pads after manufacture, in which case sensors are selected for application to pads based on the pad type they identify.

In one embodiment, the processing means is configured to receive automatically a sensor status indicator which indicates whether a sensor, or an absorbent article associated with a sensor, is newly connected to the system or is being re-connected to the system. Specifically, the sensor status indicator can be used to designate, without doubt, when a new sensor (and new pad) is being connected to a transmitter as would be the case when a subject is undergoing a pad change. This is distinguishable from the case where a sensor (and associated pad) has been disconnected from the system and is being re-connected to the system as may be the case when a carer disconnects a sensor from a transmitter to check, but not change, a subject's absorbent pad.

The sensor status is preferably determined by reference to a characteristic of a sensor status circuit on the absorbent article. The sensor status circuit may be combined with the identifier circuit or it may be provided separately. The characteristic may be determined by reference to one or more elements incorporated into the sensor status circuit. The elements may be selected from the group including capacitors, expirable components, contactless devices such as those which employ inductive coils, and memory devices including read only and programmable memory devices. Where an expirable component such as fuse is employed, the sensor status circuit cannot be re-used to designate that the sensor is associated with a fresh (un-used) absorbent article. This is because the component is designed to expire when the sensor is first used (i.e. connected to an energy source e.g. of the type found in a connectable transmitter). The sensor status is considered to be newly connected when the fuse is initially closed (i.e. in tact). When the sensor is used (i.e. connected to a transmitter having an energy source), the fuse expires and an open circuit is formed which designates that the sensor has been used (i.e. previously connected to the system).

In a preferred embodiment, the sensor status circuit includes a capacitor and the sensor status is determined to be newly connected (unused) when the capacitor is uncharged. When the capacitor has been charged, this signifies that the circuit has had previous connection to an energy source designating that the sensor has already been "used". In one arrangement, the capacitor size (e.g. in Farads) can be used to designate the sensor type or pad type. Sensor type and pad type may be distinguishable where sensors are retro-fitted to pads that do not already contain sensors. Sensors may be of different types e.g. where they have different functionality. Such functionality may include, in addition to sensing wetness or as an alternative there to, sensing one or more of temperature, pH, odour, bioanalytes and the like. The rating of the capacitor may be determined by the system by identifying e.g. the time to charge the capacitor when the sensor is initially connected to the system.

Expirable elements such as fuses are usable only with disposable sensors as they cannot be used to designate a newly connected (unused) status more than once. Other devices, such as capacitors, may be re-set e.g. by discharging. Discharging may be achieved actively or by allowing accumulated charge in the capacitor to discharge over time.

Preferably, the visual representation shows diagrammatically on a time scale one or more estimated void volumes in the absorbent article of a subject being monitored and also shows, on the same time scale, the occurrence of one or more non-wetness events specific to the subject being monitored. The one or more transmitters is preferably configured to transmit data to the processing means identifying points in time for which non-wetness event data is required. Preferably, the processing means is configured to cause e.g. a hand held device to provide a visible and/or audible and/or haptic reminder to a user to enter required non-wetness event data for a subject using the input means. Non-wetness event data may relate to e.g. unintended disconnection of a transmitter from a sensor; manual toileting of the subject; a new absorbent article being associated with a sensor (where this is not automatically communicated using a sensor status indicator); an intervention on a subject performed by a carer; the subject changing position; actuation of an actuator on a transmitter (e.g. button press); a change in data transmission or sensor connection status; the subject has fallen; and a particular sequence of sensor or transmission events, to name a few.

The input means may facilitate manual entry of non-wetness event data by one or more of: a menu list of items presented on the display means; one or more actuators on the transmitter; optically, electronically or otherwise scanning a code from a card or other reference guide; and manual entry of a code; wherein any of the foregoing are optionally performed using a hand held device.

The processing means may be configured cause an alert to be presented to a carer automatically so that the carer attends to a subject being monitored. An alert may be caused because of one or more of e.g. a risk of wetness leakage calculated by the processing means; the sensor and transmitter are disconnected; transmission has ceased; low power remains in an associated transmitter; the subject has potentially fallen; data collection has ceased; another condition detected by sensors attached to the transmitter; and an internal inconsistency condition in relation to the various data captured by the system.

The processing means may be configured to correlate automatically patterns in continence-related data and optionally non-wetness event data with one or more disease condition indicators and provide automatically guidelines to investigate the presence of a disease state. The processing means may also be configurable to receive inputs from any sensor type. This may be achieved by e.g. for a configuration period: collecting continence data from a sensor of the particular sensor type associated with an absorbent article worn by a subject; and collecting non-wetness event data pertaining to the subject; and using the collected non-wetness event data and sensor data to optimise a mathematical model for monitoring incontinence in a subject; wherein the optimised model is used to monitor incontinence in a subject wearing an absorbent article with a sensor of the particular sensor type.

In one embodiment, the system is configured for home use and includes a waste receptacle fitted with a scale. The scale determines the mass of a soiled absorbent article placed in the waste receptacle. The receptacle may also include pad type identifying means for automatically identifying a pad type for which the mass is determined by the scale. The pad type identifying means may use one or more of: a pad type indicator circuit on the absorbent article (e.g. such as described in the foregoing); scanning means scanning a barcode on a surface of the absorbent article; a pad type receiver receiving a pad type signal from a contactless transmitter on the pad; a sequence of events where disconnection of the pad from the transmitter is followed by deposition of the pad into the receptacle; and manual entry of a pad type identifier to determine pad type. Preferably the mass of the soiled pad is communicated automatically to the processing means.

In a preferred embodiment, the processing means receives multi-site continence-related data obtained from a plurality of sites where the system is used to monitor subjects for incontinence. The processing means may thus include a data compiling processor receiving the multi-site continence-related data. The system may provide a data store for storing the multi-site data, and one or more network communication elements connecting the one or more sites with the data compiling processor. The processing means may utilise data obtained from the plurality of sites to perform automatically, one or more of: verifying a mathematical model for estimating void volume; and improving or optimising a mathematical model for estimating and/or categorising e.g. void volume.

Preferably, the data store stores analysis data from the data compiling processor which may perform analysis including one or more of: identifying trends in usage of absorbent articles; evaluating care assessments for subjects being monitored; identifying trends in carer behaviour; analysing population data; identifying correlations between continence-related data, event data and other conditions applicable to a group of subjects; benchmarking performance of different continence products; and benchmarking performance of different models of continence care. Identifying trends in carer behaviour may include assessing one or more of: carer efficiency; response time; effectiveness of carer entry of non-wetness event data; and compliance with care standards.

The data compiling processor may also utilise data obtained from the plurality of sites to assess at least one of: care facility features and effect on care; resident wellbeing; and absorbent article utilisation and/or performance.

The system may be used for training care staff to perform duties including one or more of: selecting a suitable absorbent article/pad type; using the system to monitor and/or assess incontinence sufferers; timely attendance to subjects with incontinence; evaluating a condition of a subject suffering incontinence: developing a continence care plan for a subject; and evaluating effectiveness of a continence care plan.

Viewed from another aspect, the present invention provides a sensor for detecting wetness in an absorbent article, the sensor including an identifier circuit for automatic identification of one or both of a pad type associated with the absorbent article and a sensor status. In one embodiment, the identifier circuit facilitates identification of a particular pad type by reference to a characteristic of the identifier circuit. The characteristic may be e.g. resistance, impedance, capacitance, inductance, a resonant frequency or a carrier frequency associated with the identifier circuit or a potential difference, current or electromagnetic field strength measurable from the identifier circuit. In one embodiment, the identifier circuit exists in parallel with a sensing circuit on the pad. Preferably, the identifier circuit indicates the pad type by reference to a resistance value in the identifier circuit, wherein a designated pad type is associated with a designated resistance value.

The identifier circuit may alternatively/additionally facilitate determination of a sensor status as one of 'newly connected' or 're-connected' to the system, to designate sensors that are previously unused or previously used. The sensor status may be determined by reference to a characteristic of one or more elements incorporated into the identifier circuit, wherein the elements may be selected from a group including capacitors, expirable components, contactless devices, and memory devices (programmable and non-programmable). Preferably, the identifier circuit includes a capacitor and the sensor status is determined to be newly connected when the capacitor is uncharged. In one embodiment, the value of the capacitor can be use to designate a sensor type and/or a pad type. Alternatively, the identifier circuit may include a fuse, wherein the sensor status is determined to be newly connected when the fuse is intact, or closed, and is determined to be re-connected when the fuse is blown, or open, as a result of connection of the sensor to an energy source in the system (e.g. a transmitter).

This can be ascertained by visual inspection or by detection of an open circuit in the identifier circuit.

Viewed from yet another aspect, the present invention provides a method for monitoring incontinence in a subject wearing an absorbent article containing a wetness sensor coupled to a transmitter, the method including the steps of: transmitting from the transmitter continence-related data to a processing means; estimating a volume of wetness in the absorbent article; and the processing means communicating display information to a display means for display of a visual representation of estimated wetness volume with respect to time.

The method may also include the step of operating an input means to provide to the processing means time-marked non-wetness event data and causing the processing means to include on the visual representation the time location of one or more non-wetness events for a subject being monitored. Further, the method may include the step of receiving a pad type indicator for an absorbent article and calculating a risk of wetness leakage from an absorbent article based on an estimate of volume of wetness in the absorbent article and the pad type of the absorbent article. The a visual representation on the display means may also provide an indication of the risk of wetness leakage.

The method may include determining automatically when the risk of wetness leakage exceeds a pre-determined acceptable risk and/or that the estimated volume of wetness in an absorbent article exceeds a pre-determined threshold, and transmit automatically an alert to a carer for the subject being monitored.

Preferably, the method further includes the step of transferring continence-related data to an analysis processor receiving continence-related data from a multiplicity of sites and collating, packaging, extracting, correlating, integrating and/or analysing the multi-site data for use by an entity selected from a group including: hospitals, care institutions, manufacturers of absorbent articles, governments, health insurers, researchers and individuals.

BRIEF DESCRIPTION OF THE DRAWINGS

Embodiments of the present invention will now be described in greater detail with reference to the accompanying drawings which are provided by way of non-limiting example. It is to be understood that the particularity of the accompanying drawings does not supersede the generality of the preceding description of the invention.

DETAILED DESCRIPTION

Figure 1:
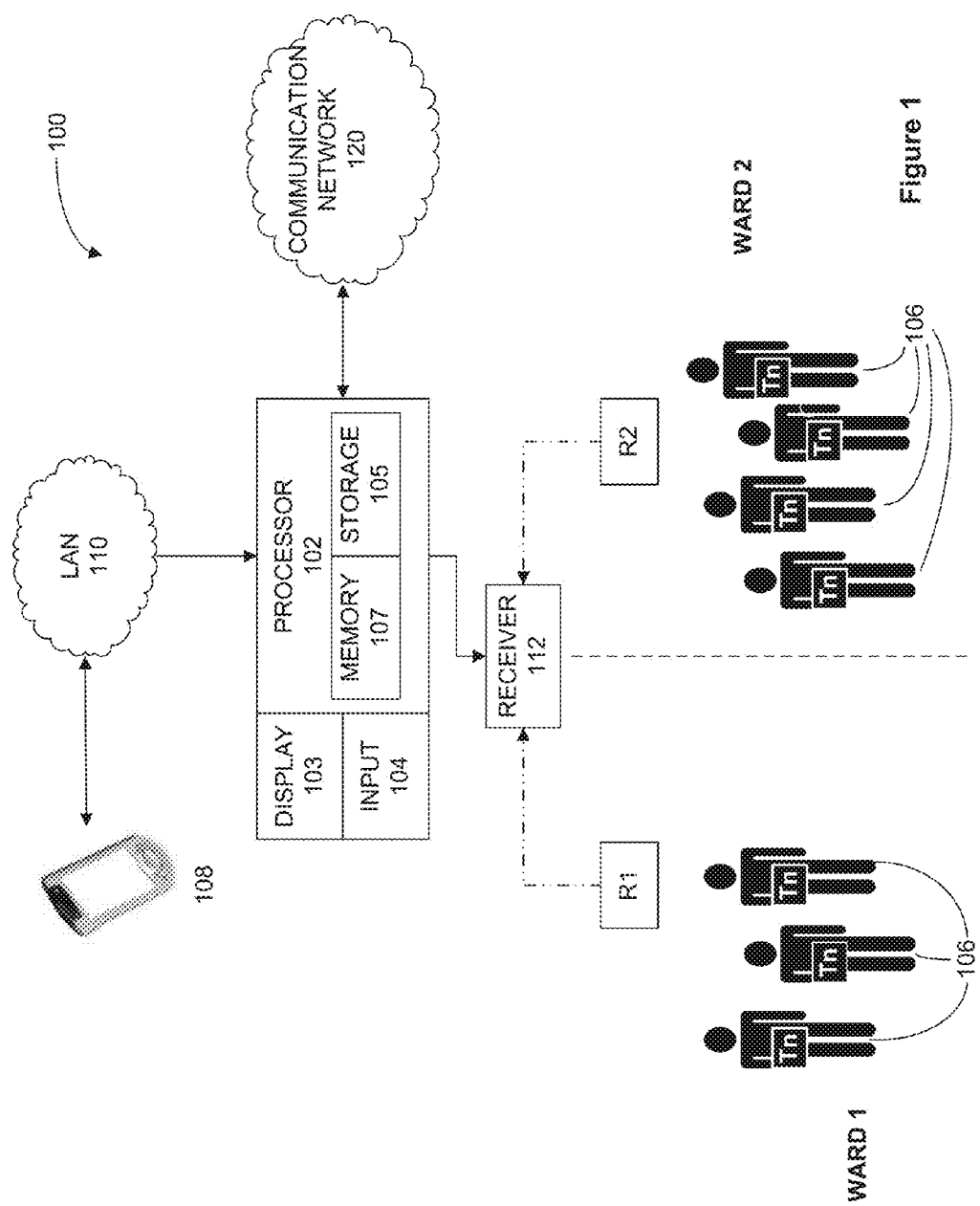
FIG. 1 is a schematic illustration of a system according to an embodiment of the invention intended for institutional use.

In most care institutions there is minimal use of technology to monitor subjects suffering from incontinence. Rather, incontinent residents or patients (referred to generally as "subjects") are typically cared for using traditional methods involving manual wetness checks. There are many drawbacks with this approach as outlined in the Background.

Administering appropriate and cost effective care is also complicated by the wide array of incontinence products which are available on the market. Different brands of pad or incontinence garment claim to provide different benefits and absorbency characteristics and it is increasingly difficult for care institutions (and individuals) to select the correct type of pad/diaper/insert or other incontinence garment for a particular subject. To some degree, purchasers of incontinence garments for institutional use are influenced by manufacturer claims and sales staff and evidently by the cost of the articles. However, little regard is had to the wearers of these garments and their incontinence behaviour in terms of how the pad is used.

To assist with pad selection, manufacturers often include an indication of the absorbent capacity of a pad. To ensure a consistent approach to determining absorbent capacity, international standard ISO 11948-1 (the Rothwell method) was devised. This is a laboratory method defining the standard for determining a pad's absorbent capacity. Notwithstanding the assistance of "pad capacity" as an indicator of pad performance, there are also design characteristics such as leg elastics, waist elastics, standing cuffs and use of super-absorbent materials which influence pad performance but these are not considered by the Rothwell method and so are not objectively considered in purchasing decisions.

Pad selection for individuals is typically determined based on a combination of: the extent of their urinary incontinence (i.e. how much an individual voids and how often), which pad size and design fits best and the level of difficulty to change the person's pad. However it has long been a challenging task to monitor a subject's continence behaviour in such a way that it reliably detects their level of incontinence and facilitates selection of a pad which is substantially matched to that behaviour. An aspect of the present invention involves a system which, in an embodiment, can assist in the decision making process for pad selection and also for determining a probabilistic indicator for when a pad ought to be changed.

Thus, in one aspect, the system of present invention provides a decision making tool for use in caring for subjects suffering from various incontinence conditions. The tool can assist carers in the allocation of pads to subjects including the size of pads required and the types of pads needed (e.g. volume capacity). This can be used on a greater scale by care institutions in procurement of absorbent pads for their residents, and supply management. Further, the tool can assist carers by providing optimised toileting schedules for residents whose incontinence condition and behaviour is assessed using the system.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components or group thereof.

Where the term "pad" or "absorbent article" is used in this specification (including in the claims), it is to be taken as a reference to all absorbent pads or absorbent articles or garments wearable by the subject including diapers, inserts, incontinence pants and the like.

FIG. 1 shows an embodiment of a system 100 for monitoring incontinence in one or more subjects 106. The system includes a display 103 under the control of processor 102 and providing a visual representation (FIG. 2) of continence-related information obtained by monitoring wetness events occurring in an absorbent article 300 worn by a subject 106. The display 103 may be provided at a monitoring station such as a nurse station in an institutional care setting. A carer responsible for the wellbeing of a subject being monitored uses the display 103 to receive alerts or to check the continence status of the subject by viewing the visual representation. The display may also convey visible reminders to carers to check the continence status of a particular subject. A loudspeaker may also provide an audible cue and a vibration element may provide haptic notification. In most institutional settings, a carer will be responsible for more than one subject and in some cases, up to six subjects, and can view the continence status of each of these subjects using a single display device by selecting from a menu, list or the like, the subject of interest.

Figure 2:
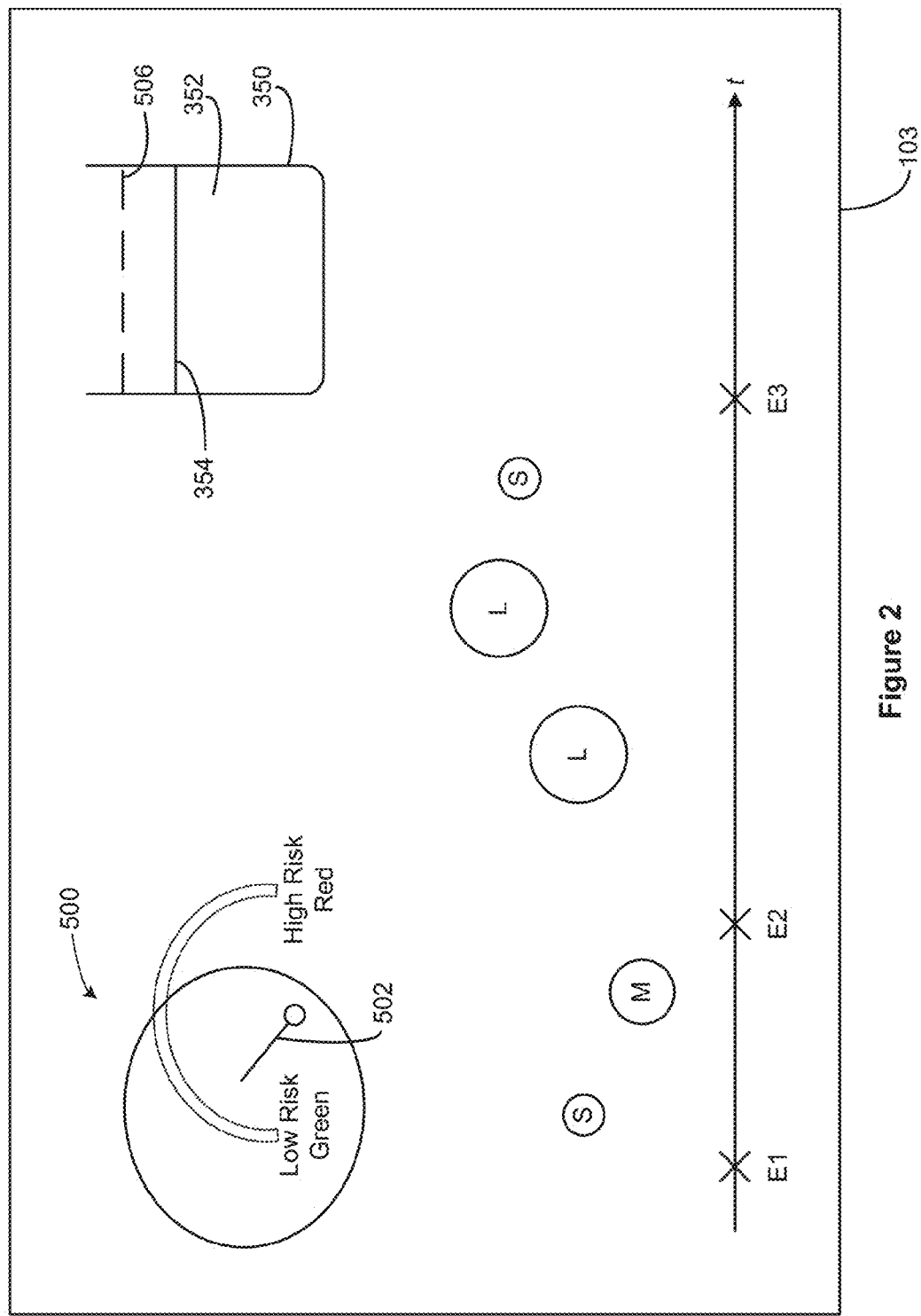
FIG. 2 is an example of a display providing a visual representation of continence-related information including estimated void volume, pad saturation and risk of wetness leakage, according to an embodiment of the invention.

Now turning to FIG. 2, display 103 is typically a screen such as a LCD, LED or other screen of the type commonly used as a computer monitor although it is to be understood that other display devices may be used. In one embodiment, there is a plurality of display devices connected with processor 102 which forms part of the processing means of the system. In one embodiment, each carer has a wireless hand held unit 108 which includes a display (i.e. screen) 103 capable of providing a visual representation of a continence status of one or more subjects who are the responsibility of that carer. In such embodiment, the processor 102 wirelessly transmits signals for the visual representation to be displayed on hand held device 108.

In one embodiment, a receiving and processing element is provided in hand held device 108 as well as an input component. The input component enables the carer to operate the device and, in certain embodiments, input data to the system. Input data may include non-wetness event data although event data may also be provided to the system by use of central input means 104 as described below. The hand held device 108 may be custom designed to operate with the system. Alternatively, it may be a personal digital assistant or similar smart mobile device having one or more applications installed which enables the device to operate as part of the inventive system. The hand held device 108 is also configured to provide visible and/or audible and/or haptic (e.g. vibration) cues or alert signals to indicate that a subject being monitored by that carer requires attention e.g. for a pad change, manual toileting, to attend to a fall etc.

The system also provides input means 104. The input means 104 may include one or more of a keyboard, mouse, barcode scanner, radio frequency device reader, touch screen, stylus or the like and enables a user of the system to enter information for use in monitoring or assessing incontinence in one or more subjects. In an institutional setting, the user is typically a carer or staff member responsible for entering information about residents (subjects) being monitored using the system. When the system is initially used to commence monitoring a subject, information entered using the input means 104 typically includes the name and bed/room location of each individual subject being monitored. Demographic data such as the subject's age, gender, medical history, family history and the like may also be entered or obtained automatically from existing electronic patient records with which the system may communicate and/or interoperate.

The input means 104 may also used by a carer or other staff member to enter non-wetness event data including observation data which is used by the system to optimise mathematical models employed by the processing means and also for preparation of toileting schedules. In a non-institutional setting (i.e. residential home use), the subject himself may provide inputs to input means 104. Alternatively, where the system is deployed for residential home use there may be a family member who assumes the role of "carer" and who provides non-wetness event data using the input means 104.

In one embodiment, each subject is allocated a transmitter $T_n$ which is then associated in the system with the subject $106_n$ using the input means 104 and processor 102. The transmitter $T_n$ contains a wireless transmitter/receiver, a processor and memory and couples with a sensor which is embedded in or attachable to an absorbent article, beneath a top layer of the pad (typically a "dry" layer). The coupling between the transmitter and the sensor may be via electrical contact or the coupling may be contactless e.g. using inductive coupling or the like.

Figure 3:
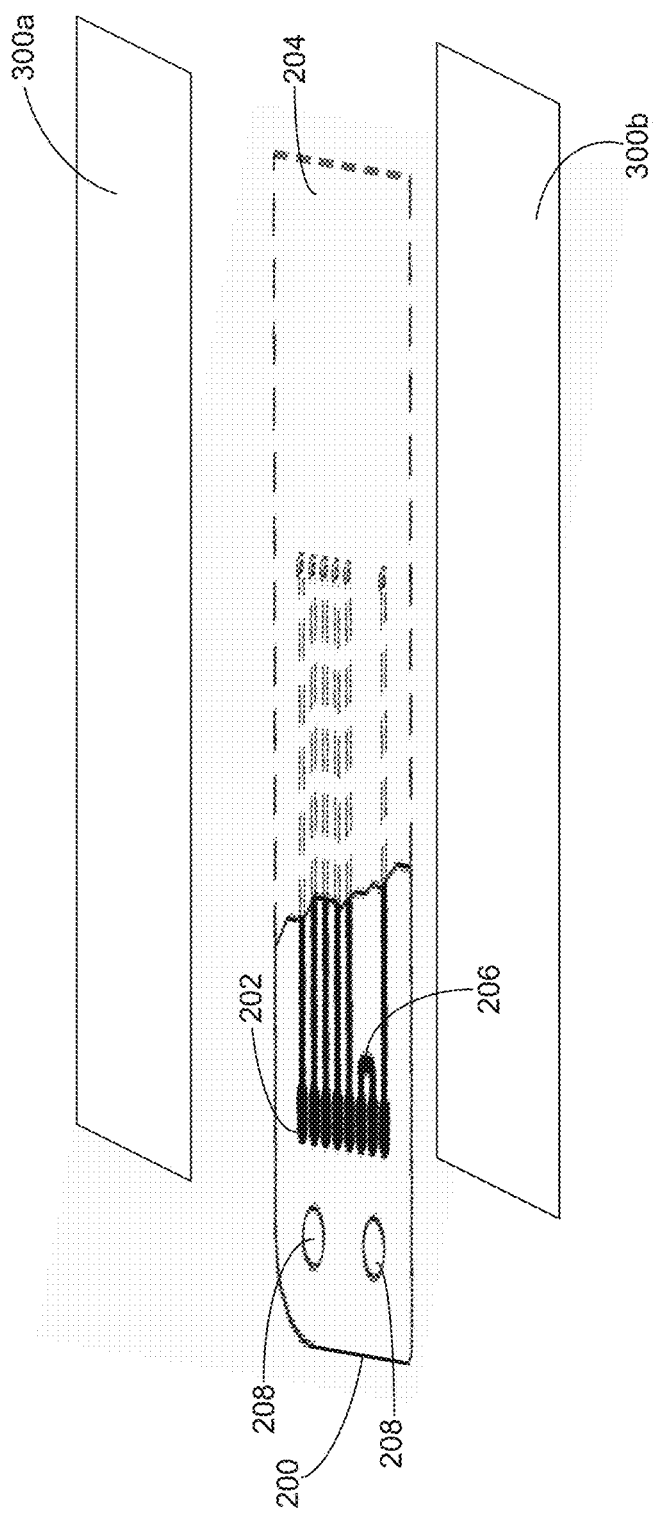
FIG. 3 is a schematic illustration of a sensor of the invention between layers of an absorbent article.

Processor 102 receives signals from the one or more transmitters $T_n$, each of which is associated with a subject $106_n$, being monitored by the system. Each transmitter $T_n$ is configured to transmit signals containing continence-related data for the subject $106_n$, obtained over time from a continence sensor 200 associated with an absorbent article 300 worn by the subject (FIG. 3). Each of the transmitters may be configured to transmit data continuously, or to store time marked continence-related data from the sensor and forward the data periodically to the processor.

Processor 102 is in communication with receiver 112 which receives signals from transmitters $T_n$ either directly or indirectly via repeaters R1 and R2. As can be seen in FIG. 1, processor 102 is employed in an institutional care setting where residents in two separate wards, Ward 1 and Ward 2, are monitored. Each ward or area of the institution may be fitted with a respective repeater to ensure adequate signal strength during relay of signals from the transmitters $T_n$ associated with individual subjects 106 to the processor 102. In the example illustrated, Ward 1 utilises repeater R1 while Ward 2 utilises repeater R2 to ensure adequate signal strength to receiver 112. In this arrangement, transmitters $T_n$ may be low power transmitters requiring less frequent access to battery replacement or re-charging.

It is to be understood that the functionality of processor 102 may be contained within a single processing element, e.g. located at a central station in a ward or the like. Alternatively, processor 102 may be provided in the form of a mobile processing device of the kind commonly employed in personal digital assistant and other hand held or mobile computing devices. As a further alternative, the functionality of processor 102 may be a distributed over a combination of central and remote devices wired or connected wirelessly with the central component of processor 102. In a preferred embodiment, processor 102 is also in communication with WAN (wide area network) 120 through which continence-related data and event data may be transmitted to other devices such as data compiling processors.

Wireless communication may be implemented over a LAN (local area network) 110 such as a paging, Wi-Fi or ZigBee network having infrastructure specific to the institution in which the system is being used. In such arrangement, the mobile or hand held devices may be custom designed to work with the inventive system. In other embodiments, instead of using a LAN 110, the public mobile telephone communications networks may be used to convey signals from processor 102 to hand held units 108 in the possession of carers. In such arrangement, the hand held units may be mobile phones of the kind sold to the general public. Smart phones or similar devices may be used, with applications installed thereon for use with the inventive system, enabling input of patient data and other non-wetness event data, displaying the visual representations of a subject's continence-related information and the like. Various communications protocols may be adopted for transmitting signals to hand held devices used by carers. Examples of various architectures over which the system may be deployed are provided below.

A volume estimator uses continence-related data from the sensor associated with a subject together with a mathematical model derived from correlations between actual observations (i.e. non-wetness event data pertaining to e.g. actual wetness volume as determined by weighing a soiled pad after changing) and previously obtained sensor data to estimate the volume of wetness in an absorbent article. The volume estimator may estimate discrete volumes of individual wetness events detected in the absorbent articles being monitored. The estimates of discrete volumes may be quantified as an actual volume in milliliters. Alternatively, the volume estimate may be categorised so that individual wetness events are identifiable as small, medium or large volume amounts. Alternatively/additionally, categorisation may provide for identification of wetness in various events as being urine, faecal, or a mix of faeces and urine. Ideally, the categorisation provides for the identification of conditions in terminology which the care-giver understands and finds useful in order to decide the appropriate action to take with the resident according to their specific condition.

Alternatively/additionally, the volume estimator may estimate cumulative wetness volume in an absorbent article. The cumulative volume may be quantified in milliliters or alternatively/additionally, the cumulative wetness volume estimate may provide for categorisation such as damp, wet or soaked as indicators of saturation or cumulative volume. Alternatively/additionally, the cumulative wetness volume estimate may provide for an indication to a user of when the cumulative volume of wetness in the pad is below a minimum threshold amount, between a minimum and a maximum threshold amount or above a maximum threshold. Volume estimate indicators, categorisations and the like may be presented to the user on display 103.

Volume estimation has utility in guiding carers in respect of when a pad requires changing or is likely to require changing which helps to improve the comfort and safety of subjects under their care. Estimating cumulative volumes of wetness in the pad assists with future allocation of pads for a particular wearer, since large volume capacity pads may not be necessary for subjects whose cumulative wetness volumes may be categorised as "small" and shifting to a pad having a lower volume rating may provide cost savings. Conversely, where a subject's risk of wetness leakage and/or cumulative volumes are high or exceed an acceptable threshold, that subject may be identified as requiring more frequent pad changes and/or allocation of a higher volume capacity pad for future usage.

In one embodiment, individual void volumes may be calculated by determining the difference between the cumulative wetness volumes in the article between individual voids. Such a method is described in International patent publication WO2007/128038, the entire disclosure of which is hereby incorporated herein by reference. Alternatively, the volume of individual wetness events may be determined by application of sensor data to a pre-determined mathematical model capable of determining those volumes, preferably without monitoring the progressively increasing cumulative volume of wetness in the pad. The volume estimator may be incorporated into a processor located at a central monitoring station, or a processor on the individual transmitters $T_n$ or another processor providing processing functionality within the system.

Estimates of wetness volume are indicated diagrammatically on a visual representation provided on a display means 103. The system is configurable to send automatically an alert to a carer responsible for that subject when the estimated cumulative wetness volume exceeds a threshold volume $V_{TH}$, and/or when a risk of wetness leakage from the pad, as calculated by processor 102, has exceeded a pre-defined threshold $P_R$ (e.g. 80%). FIG. 2 is a schematic example of a visual representation according to an embodiment of the invention in the form of a chart showing diagrammatically void volumes estimated by processor 102 after detection by sensor 200 of a number of wetness events. In the chart, time is shown on the x-axis. The occurrences of individual voids as detected by the sensor are shown in circles, where the area of the circle is proportionate to the estimated volume of the void as determined by the volume estimator. For example three circle sizes may be used. A small (S) circle designates a void of less than e.g. 100 mL. A medium (M) circle designates a void of e.g. 100 mL to 200 mL. A large (L) circle designate void greater than e.g. 200 mL. In one embodiment, a red circle denotes a void inside the absorbent article as determined by sensor 200 whereas a green circle denotes an observed toileting event (this is manually entered non-wetness event observation data) the actual volume of which is estimated or measured by the carer (or subject) and provided to input to the system using input means 104.

Display 103 also shows a visual representation of a container 350 containing liquid 352 filling the container to a fill line 354. The level of fullness of the container indicates the degree of saturation of the subject's pad and provides the carer with a visual indicator of how full the pad is. The container may also show a level 506 at which the pad becomes saturated. This level may indicate e.g. the absorbent capacity of the pad or a threshold volume at which care protocols require the pad to be changed. Alternatively, the visual representation may indicate a threshold volume $V_{TH}$ which, when met or approached by the cumulative volume in the pad as estimated by processor 102, causes an alert to be sent to a carer to attend to the subject and check/change the pad. Display 103 also shows an example of a "risk of wetness leakage indicator" as in the form of a gauge 500 with a needle 502 which moves according to the risk as calculated by processor 102. In a preferred embodiment, the gauge or parts of it are coloured to assist carers in ascertaining the risk of leakage. Thus, where there is low risk of leakage from the pad the gauge is coloured or shaded green whereas where there is a high or critical risk of leakage, the gauge is coloured or shaded red. Alternatively, text indicators may be used, as illustrated.

Each pad used with the system has a known "type" which is used by the processor to calculate a risk of wetness leakage. Pad type typically indicates the size (i.e. absorbent capacity) of the pad as may be determined e.g. using the Rothwell method. The pad type indicator for a particular pad may be provided to processor 102 manually e.g. by a carer using input means 104 to enter the pad brand and size (e.g. Small, Medium or Large). Alternatively, processor 102 may use a look-up table or other reference file in memory 107 to ascertain the absorbent capacity of the pad being used. However in a preferred embodiment the pad type is communicated automatically to processor 102.

FIG. 3 is a schematic illustration of an embodiment of a sensor 200 positioned between layers 300a,b of an absorbent article 200 used with the inventive system. In the embodiment illustrated, the sensor is a resistive sensor having a series of silver sensing electrodes 202 printed onto a polyester substrate 204. The sensor 200 is inserted between a top ("dry") layer and absorbent layers 300a,b of an absorbent article wearable by a subject monitored using the system. Preferably, a sensor 200 is inserted between these layers as part of the manufacturing process for absorbent articles, before they are packaged and distributed. However, the sensor may alternatively be fitted to absorbent articles after manufacture. Installation of a sensor 200 into absorbent articles 300 may be performed after manufacture manually, using the aid of an insertion tool, or a peel off adhesive backing on substrate 204 or automatically using insertion apparatus. Connectors 208 protrude from pad 300 for attaching the sensor to transmitter T, which has internal circuitry for connecting with sensing electrodes 202 to facilitate transmission of sensor signals to processor 102, or processing within the transmitter T. Contactless coupling between the sensor 200 and transmitter T is also contemplated.

The sensor 200 illustrated in FIG. 2 monitors changes in resistance between the electrodes 202 to identify the presence of wetness in the absorbent article 300. When the absorbent article is substantially dry, resistance between electrodes in the sensor is maximal. When a wetness event occurs, moisture from exudate in the pad completes a conductive circuit between the electrodes and the resistance of the circuit decreases. The magnitude of the change in resistance together with the rate and duration of change is detectable by a transmitter T couplable with the sensor which, in use, transmits a continence-related data signal to processor 102. However, the sensor could use a range of other indicators to generate a continence-related data signal. These may include, for example, changes in temperature, capacitance, inductance, impedance, presence of biological specimens, gases etc.

In a preferred embodiment, continence sensor 200 is designed for use with a particular pad type and thus includes an identifier circuit 206 for automatically identifying that pad type to processor 102 during use. In the embodiment illustrated, identifier circuit 206 exists in parallel to sensing electrodes 202 and has a characteristic value (e.g. of resistance) which an be correlated with a pad type indicator.

The characteristic value of the identifier circuit 206 may be referenced in a look up table or other reference stored e.g. in memory 107 associated with processor 102 to ascertain the absorbent capacity for that pad type. Alternatively, the characteristic value may be referenced in a national, international or industry standard which manufacturers observe and thus, any pad manufactured with a particular absorbent capacity (as may be determined e.g. using the Rothwell method) can be assumed to have a designated resistance value built into its identifier circuit. For manually inserted sensors, the sensor 200 is selected according to the type (i.e. absorbent capacity) of the pad.

While identifier circuit 206 illustrated in FIG. 2 has a predetermined resistance value for a designated pad type, it is to be understood that other circuit characteristics may be employed to designate pad type. These may include for example impedance, capacitance, inductance, a resonant frequency or a carrier frequency associated with the identifier circuit in the continence sensor, and/or a potential difference, current or electromagnetic field strength measurable from the circuit.

In another preferred embodiment, continence sensor 200 includes a sensor status identifier for identifying automatically when a pad has been newly connected to the system, as may be distinguished from re-connection of a pad that has already been used/connected with the system. This overcomes the problems associated with manual entry by care staff of data indicating when a pad change has occurred. Naturally carers are very busy and data entry compliance levels can be low. Thus, care staff are prone to a) forget to provide an input to the system indicative of a fresh pad being applied to a subject; or b) when entering this data 'after the fact', enter the wrong time at which the fresh pad was applied. Erroneous or omitted data of this kind can lead to lower accuracy in toileting schedules derived by the system, errors in bladder diaries provided by the system, and errors in volume estimates provided by the volume estimator (since application of a fresh pad to a subject re-sets the cumulative volume to 'zero') and erroneous optimisation when the data is employed to optimise mathematical models used by the system. A further advantage of the sensor status indicator is that unintended or intermittent disconnections of the sensor from the system (e.g. the transmitter) do not cause false "pad replacement" data to be collected by the system.

In one embodiment, the sensor status is determined by reference to a characteristic of a sensor status circuit that is connected to the sensor. The characteristic may be determined by one or more elements incorporated into the sensor status circuit and the elements may be e.g. capacitors, expirable components such as a fuse, contactless devices and memory devices.

Figure 7:
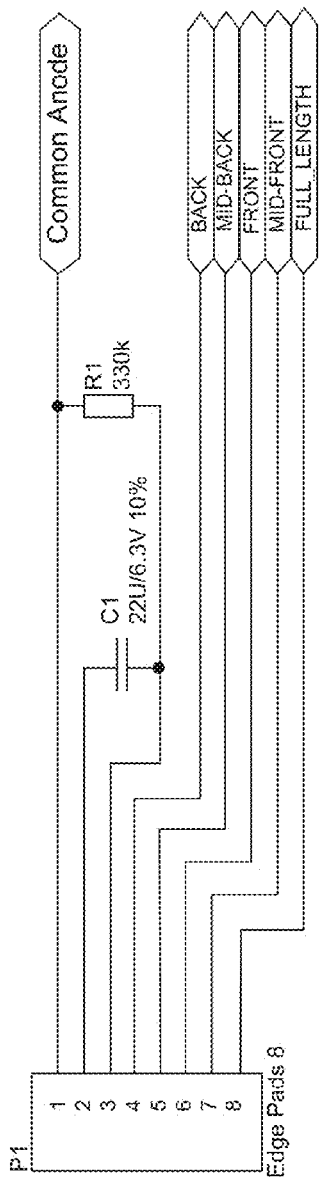
FIG. 7 is a schematic illustration of an electronic circuit provided on a sensor device according to an embodiment of the invention for use in identifying pad type and sensor status.

Referring to FIG. 7, there is provided an example of an identifier circuit combined with a sensor status circuit for use in an embodiment of the invention. This circuit is shown between pins 1, 2 and 4 of connector P1 which connects the sensor (and pad type/status identifier circuit) with the transmitter. In this circuit, resistor R1 is varied according to each pad type, where 'pad type' may designate volume capacity or make/model of an absorbent article used with the system. The indicated value of R1 being 330 k Ohms is demonstrative of one such pad type which may have e.g. 200 mL capacity.

Capacitor C1 may also vary according to e.g. pad type or sensor type (where sensors are not embedded in pads as part of the manufacturing process). In embodiments where different sensors provide different functionality and may be offered at different price points, it may be desirable to provide a sensor identifier which can be used to a) ensure an appropriate sensor type is being selected for application to a particular pad type and b) for automated charging or funding of the subject's care, or funding analysis. In the embodiment illustrated in FIG. 7, C1 has a value of 22 microfarads which demonstrates just one suitable capacitor value.

The combined pad type and status identifier circuit illustrated in FIG. 7 is intended for use with a monitoring device which, in a preferred embodiment, is incorporated into transmitter T. It is desirable that the monitoring device contain a circuit of the type illustrated between pins 3 and 4 of connecter P1 in FIG. 8. In this arrangement, the monitoring device circuit of FIG. 8 interfaces with the combined pad type and status identifier circuit of FIG. 7 in the manner indicated in Table 1 below.

TABLE 1

| P1 on Transmitter/Monitoring Device | P1 on Incontinence Sensor |
|---|---|
| Pin 1 | No connection |
| Pin 2 | Pin 1 |
| Pin 3 | Pin 2 |
| Pin 4 | Pin 3 |
| Pin 5 | Pin 4 |
| Pin 6 | Pin 5 |
| Pin 7 | Pin 6 |
| Pin 8 | Pin 7 |
| Pin 9 | Pin 8 |
| Pin 10 | No connection |

Figure 9:
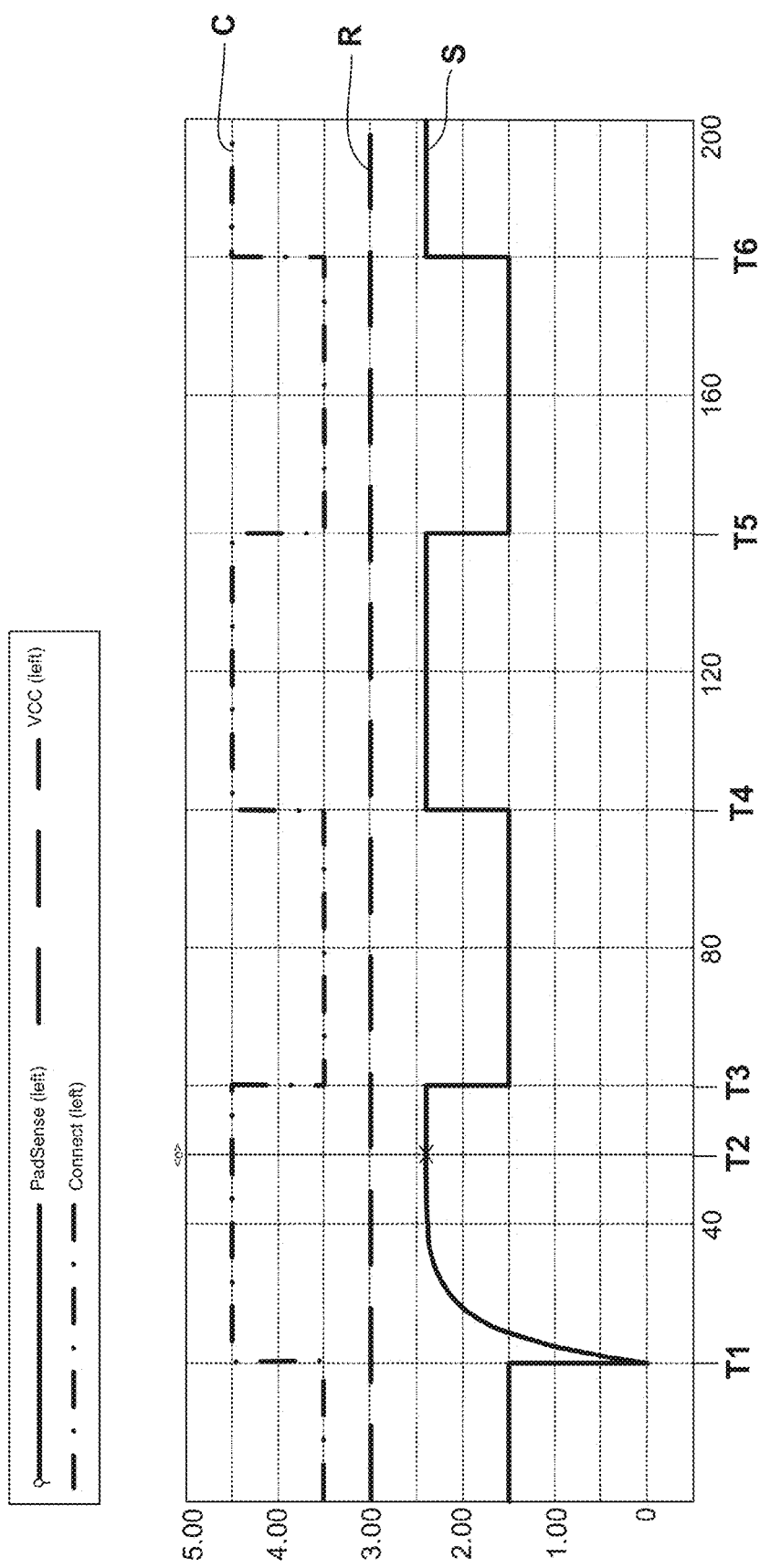
FIG. 9 is a schematic illustration of signal data obtained from the monitoring device referred to in FIG. 8.

FIG. 9 is a timing diagram showing signal values indicative of changes in the combined pad type/sensor status indicator circuit (indicated at S). In FIG. 9, R represents the reference voltage of a monitoring device/transmitter with which the sensor is connected; C represents a signal indicating whether the sensor is in a 'connected' or 'disconnected' status as detected by the monitoring device; and S represents the pad sense signal received at the input of the monitoring device which is used to detect whether the connected pad/sensor is 'used' or 'unused' (i.e. newly connected or reconnected).

Prior to connection to a sensor, the pad sense input to pin 4 of the monitoring device is biased to 1.5 volts, as divided by resistors R1 and R2 across a reference voltage of 3 volts. Prior to connection, C1 is uncharged (0 volts). When a sensor associated with a pad is newly connected to a transmitter containing the monitoring device, (at 20 seconds marked by T1 in FIG. 9) C1 pulls the pad sense input to pin 4 down to 0 volts. As C1 charges, the voltage at the pad sense input slowly increases and the voltage drop across C1 (measurable at the pad sense input) approaches the stable voltage measurable across the resistor network comprising R1 and R2 of the monitoring device, and R1 of the sensor circuit. In the embodiment illustrated, when the capacitor is charged the resting voltage is approximately 2.4 volts indicated at T2 in FIG. 9.

The time taken for the pad sense input to reach resting voltage (i.e. T2 minus T1) can be varied by varying the value of C1. In the embodiment illustrated, T2 minus T1 is approximately 30 seconds. The charge time may be used to designate the type of the sensor (e.g. an expensive sensor or a cheap sensor, a sensor for sensing wetness only, a sensor for sensing temperature, pH or the presence of a gas, or particular substance in the urine/faeces).

Ideally, the system includes processing means for processing the pad sense line to identify when a new sensor/new pad has been connected to the system. Ideally this is done by software executed by a processor on the monitoring device/transmitter although it is to be understood that detection may be achieved by hardware on the monitoring device/transmitter, or using software or hardware associated with a processor at a base station or located elsewhere in the system.

In a preferred embodiment, a processor on the monitoring device/transmitter identifies the voltage dip below 1.5 volts occurring at T1 as being indicative of fresh connection of a new, unused pad to the system (since the voltage dip is caused by previously uncharged capacitor C1 becoming charged). The monitoring device processor then determines from the resting voltage of 2.4 volts, the pad type, since the resisting voltage is determined by the value of R1 of the sensor circuit (together with R1 and R2 of the monitoring device which do not vary). Different values of R1 on different sensor circuits will change the resting voltage reached at about T2 which is indicative of a different pad type being connected to the system.

Disconnection of the sensor from the system is shown at T3 of FIG. 9 with the pad sense input decreasing back to the bias voltage of 1.5 volts. This is detectable by the processor within the monitoring device (or elsewhere) and identifiable as disconnection of the sensor (and pad with which it is associated) from the system. The disconnection may be inadvertent, or to enable a carer to check the pad, or the result of incorrect attachment of the sensor to the transmitter. The next change on the pad sense input at T4 will indicate whether a used pad/sensor combination is being connected (i.e. the same pad/sensor being re-connected), or a new, previously unused pad/sensor is being connected. In the example shown at T4 the voltage rises directly to the resting voltage of about 2.4 volts. Since there was no dip below the bias voltage, the processor on the monitoring device is able to confirm that the pad/sensor is already used, and can also confirm the pad type, as may be established by the resting voltage reached. This suggests re-connection of the same pad to the system. The same sensor is disconnected at T5, and reconnected again at T6. These disconnections and connections are analysed by the monitoring device processor and used to provide continence data to the system indicative of when a pad/sensor is replaced, and the type of the pad or pad/sensor combination.

Figure 8:
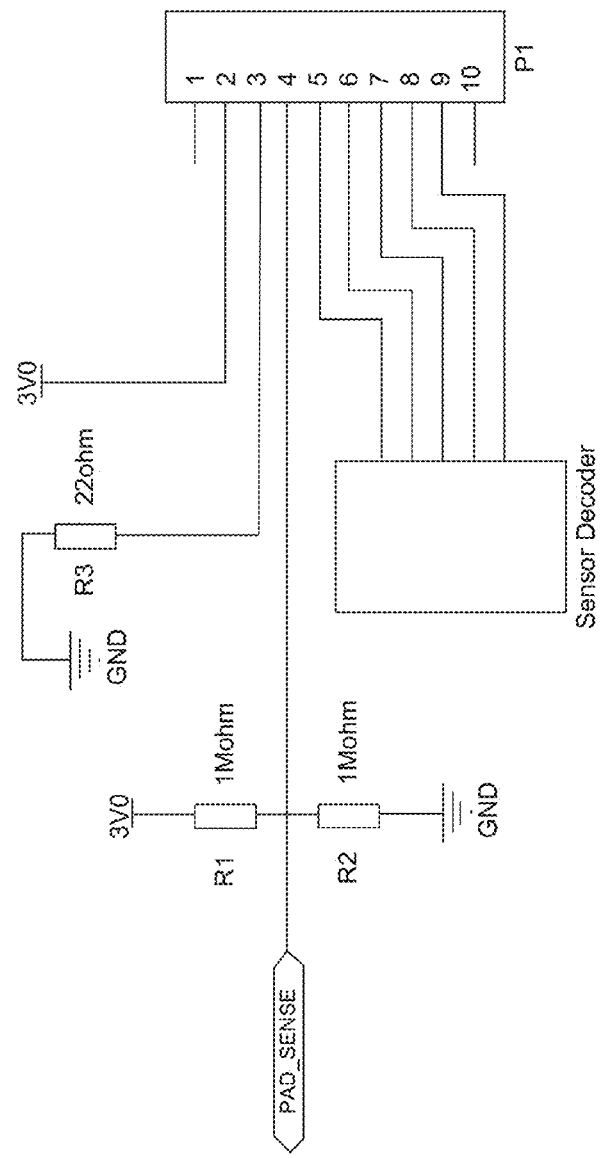
FIG. 8 is a schematic illustration of an electronic circuit provided in a monitoring device or transmitter to which the sensor is attached during monitoring.

The circuits described in connection with FIGS. 7 to 9 are re-settable circuits in that the capacitor can be left to discharge over time, or intentionally discharged to re-set the sensor status circuit. Natural discharge may occur e.g. over about 24 hours when the sensor is not connected to an energy source. Thus natural discharge is unlikely to affect the performance of the circuit while it is in use on a subject.

It is to be understood that although one example of a pad type identifier circuit and a sensor status identifier circuit has been provided in detail, other circuits may be used which employ different active and passive components. In one arrangement, a fuse or low rating resistor may be employed which burns out to form an open circuit when a small current is received by the identifier circuit upon connection of the sensor to the monitoring device. The act of burning the fuse or resistor can be controlled by the monitoring device which, upon sensing the open circuit formed by the fuse/resistor burning out, processes a previously unused pad/sensor being attached. Upon re-connection, the open circuit remains open which enables the monitoring device to detect that the pad/sensor has been used previously.

In another arrangement suitable for contactless connection between the sensor and the transmitter/monitoring device, the P1 connector on the sensor may be replaced with an inductive coil and the monitoring device may use near field magnetic induction techniques to couple the sensor to the monitoring device. In this arrangement, as the capacitor charges, current flow in the induction coil will increase to a value that correlates with the size or type of pad/sensor being used.

In yet another arrangement, a memory device may be used on the sensor. The memory device may be read only memory (e.g. PROM. EPROM, EEPROM, etc). and used to identify when an unused or used pad/sensor combination is being connected to the system by providing each pad/sensor combination with a unique identifier. For each sensor, the memory would be pre-programmed at manufacture with a unique identification code. The code also contains information indicative of the pad type wherein a header of the code may indicate manufacture and other segments of the code may indicate volume capacity or model number. The monitoring device communicates with the memory on the sensor when the sensor is connected, and observes the unique identification code. The unique identification may also be communicated to a remote processor for billing or stock control. If the monitoring device has not observed connection with a sensor having the received unique identification code within e.g. the last 72 hours then it identifies the pad/sensor as unused. However, if the unique identification code has been observed by the monitoring device during that period then the pad/sensor combination will be deemed to be 'used'.

A unique identification code may also have utility in tracking information about product usage and for post-marketing surveillance, as well as for meeting some regulatory requirements. A unique identification code may also be used to control access to the system, wherein only products having a particular code type are able to operate with the monitoring device and other aspects of the system.

In another embodiment, electronic programmable memory may be used (e.g. EEPOM, Flash, etc) on the sensor for the purpose of unique identification. In this arrangement, the memory is initially programmed at the manufacturing stage with a unique identification code and a blank security code. The unique identification code contains information pertaining to pad type and may also identify e.g. manufacturer, model number, batch number etc. The monitoring device communicates with the memory when connected to the sensor. If the security code is blank, the monitoring device establishes that the pad/sensor is unused. The monitoring device then writes a unique security code to the memory on the sensor. If the security code is recognised by the monitoring device after a subsequent disconnect/connect cycle, then the monitoring device identifies the pad/sensor as being a 'used device' i.e. one which has been previously connected to the system. The unique identification code can be used for a range of purposes in addition to monitoring the status and type of the pad/sensor, as has been outlined in the foregoing in connection the unique identification codes employed by read only memory devices.

It is to be understood that the sensor status indicators and 'type' indicators and the particular circuit arrangements described and contemplated in the foregoing have application in a range of products, particularly consumable products employed in a range of environments in healthcare and elsewhere. For instance, status identification may be utilised by patient monitors to confirm that electrodes or other body contacting elements of medical devices or monitors have not been used previously or if they have, that they have been sterilised and re-set (e.g. by discharging a capacitor or re-setting a programmable memory). A similar approach can be taken to tracking patient equipment such as beds and tables which require cleaning between allocation to different patients. In particular, Contactless determination of the 'status' and/or 'type' of such assets may prove useful in the field.

Outside of the patient care industry, 'status' information may be used for any consumer product. One example is for coffee capsules which are designed for one use only. A status indicator circuit on such coffee capsules could be used by coffee machines to identify automatically, when a capsule is a fresh capsule, or a used capsule.

Based on the pad type indicator and continence-related data collected during wearing of a pad by a particular subject, processor 102 calculates a risk of wetness leakage from the absorbent article. The risk of wetness can be evaluated by fitting sensor data and non-wetness data to logistic models of the form e.g.

$$\text{logit}(p_n) = \alpha + \beta u + \gamma_1 x_1 + \gamma_2 x_2 + \ldots \gamma_k x_k$$

Where $p_n$ is the probability that a pad n has no leakage at a urine mass u and logit $p_n$ is the natural logarithm of the odds $p_n/(1-p_n)$ for no leakage. Also, $x_{n1}, x_{n2}, \ldots x_{nk}$ are for pad n the values of k variables connected to product features such as e.g. $x_{n1}$=Rothwell capacity; $x_{n2}$=coefficient of variation for Rothwell capacity measurements etc. The coefficients $\alpha$, $\beta$, $\gamma_1$, $\gamma_2$, $\ldots \gamma_k$ are parameters which may be estimated and tested using clinical evaluation methods for leakage performance for particular pad types and fitting a logistic model to the data obtained e.g. of the form:

$$\text{logit}(p_n) = \alpha_n + \beta u$$

Alternatively, mathematical models for assessing risk of wetness leakage can be determined directly by experimental methods correlating sensor data profiles and actual observations of leakage performance in pads collected over a population of users of that particular pad type. Demographic information such as age, gender and health indicators may also be factors which influence the mathematical model. Thus risk of wetness leakage is typically a probabilistic indicator which, based on the known capacity of the pad (as ascertained from the pad type identifier) and the volume of wetness accumulated in the pad as estimated by the volume estimator, can be used by carers as a guide to when a subject is likely to require a pad change. This can, in turn, be used by carers to select an appropriate pad size, based an acceptable level of risk of pad leakage that the carer will take on.

Preferably, the risk of wetness leakage calculated by processor 102 is calculated dynamically using continence-related data obtained in real time from a sensor in an absorbent article worn by the subject. Thus, the calculated risk is altered as new data are received from the transmitter associated with that subject.

Providing an indicator of risk of wetness leakage is more useful than merely transmitting an alert to carers when a wetness event has occurred (although this alert system may also be implemented with the instant invention) as it gives carers a quantitative guide. If the risk of leakage is indicated as low (e.g. less than 10%), then carers can elect not to check or change the pad. If the risk of leakage is indicated as high (e.g. more than 70%) then carers may elect to manually inspect and/or change the pad.

As well as transmitting continence-related data signals obtained from the sensor 200, the transmitters $T_n$ are configured to transmit data to processor 102 identifying points in time for which non-wetness event data is required (i.e. a required non-wetness event data signal). This may be achieved by transmitting a time stamped signal to processor 102 which is distinct from the continence-related data signal. Alternatively, the continence-related data signal may be marked with non-wetness event indicators identifying times during the monitored period for which non-wetness event data are required.

Non-wetness event data is non-sensor derived data pertaining to the subject being monitored which, in most cases, is likely to influence that subject's continence behaviour. Non-wetness event data is typically provided to the system by carers using input means 104 (either using hand held units 108 or central input means) and can include a range of observational data and factors specific to the subject 106 being monitored as well as the performance of the sensor 200 and/or transmitter T to enhance incontinence care, assessment and management. Non-wetness event data includes e.g. the mass of a soiled pad as determined by weighing prior to disposing of the pad after a pad change. The mass of the pad is used by the processor, once entered by the carer, to determine the actual volume of wetness in the pad. The actual volume, as determined by weighing the pad, can then be used by processing means in the system to optimise the mathematical model used by the volume estimator to estimate void volume during monitoring thus weighing need not be performed.

In one embodiment, each of the transmitters $T_n$ is configured to notify the system automatically, when the transmitter has become disconnected from the sensor. This may indicate that a pad change has occurred, or that there is an intermittent connection between the sensor 200 and the transmitter device T. An intermittent connection may be determined automatically based on a sequence of transmission events. For instance, if a processor device in the transmitter T detects a disconnection/reconnection with the sensor 200 on 5 occasions in a 60 second period it may transmit automatically a notification to processor 102 and/or append a marker to the time marked required non-wetness event signal indicating that the transmitter/sensor connection is loose or unreliable. Preferably the transmitter T also identifies to processor 102 automatically where there has been a change in transmission or connection status.

In a preferred embodiment, the visual representation for each subject includes one or more visible markers for the time location of required non-wetness event data, as communicated by the transmitter $T_n$, preferably on the same time scale as the estimated wetness volumes referred to above. The time locations of non-wetness events are shown as E1, E2 and E3 in FIG. 2. Processor 102 uses the required non-wetness event data signal from a remote transmitter $T_n$ to provide a visual and/or audible reminder to a carer to enter required event data for the subject being monitored. The reminder may be provided by way of a transmission to a pager or hand held unit 108 causing the device to vibrate and/or display a reminder message and/or provide an audible message/cue. Alternatively the reminder may appear on a display 103 at a central monitoring station housing processor 102 or a processing device performing various tasks of the system processing means. Alternatively/additionally the reminder may be transmitted to the carer using a paging or other mobile communication device/system. The reminder may be communicated to the carer in real time, or it may be viewed by the carer at a time of greater convenience, e.g. at the end of a shift before change over, during a quiet period (e.g. when residents are resting or sleeping) or the like. After receiving a reminder that non-wetness that event data is required, the carer is duty bound to supply the data to the system.

A carer (or the subject him/herself in the home setting) may use input means 104 for manual entry of non-wetness event data. This may be achieved by using e.g. a mouse and/or keyboard and/or touch screen device. The input means 104 may be operated to select items presented on display 103 and enter data. For example, when the carer selects a non-wetness event marker (e.g. E1) on the visual representation a drop down menu may appear from which the carer selects the nature of the event (e.g. patient reposition). Alternatively, the carer may provide event data directly to the transmitter T by a sequence of button presses on the device which are designated for common events (e.g. fluid intake for E2, manual toileting and pad change for E3). Alternatively/additionally, the carer may use hand held device 108 to enter event data in real time e.g. by using a stylet or touch screen on the device. Event data may be selected from a list or may be user defined (or a combination of these). The input means 104 may alternatively/additionally include a device for optically, electronically or otherwise scanning a code from a card or other reference guide which lists typical events. Similarly the carer may manually enter a code corresponding to a particular event type using a keypad or the like on hand held device 108 or input means 104 at a central monitoring station.

The transmitter T may identify to processor 102 when there has been manual toileting of the subject. This may involve the transmitter T appending a marker to the time marked non-wetness event signal upon the carer or the subject pressing a button or other actuator on the transmitter T when manual toileting has been completed. The time of other interventions performed by the carer may also be recorded by a button press or other input to the input means 104. These may include food or fluid intake, intake of medication, movement observations, changing the position of the subject, or admittance (or exit) of visitors, leave from the care institute or the like.

In a preferred embodiment, the sensor 200 includes means for detecting other indicators of wellbeing of the subject. These may include means for detecting biological indicators in exudate from the subject, temperature and e.g. movement of the subject. Alternatively or additionally the transmitter T may be fitted with sensing means for further monitoring wellbeing of the subject. Thus, the remote transmitter T may include e.g. a position tracking device (such as GPS) and/or one or more motion detectors such as an accelerometer or a pressure transducer providing an indication of movement of the subject. Such detectors may be configured to detect wandering or falls (e.g. by identifying rapid movements) the existence of which may be communicated in real time to processor 102 for notification to a carer. The remote transmitter T may also include the means for monitoring vital signs such as ECG, blood glucose meter, spirometer, blood pressure monitor, pulse oximeter, etc. When these conditions are detected early and notified to carers they can enable carers to administer prompt care to subjects as necessary.

Preferably, processor 102 is configured to transmit an alert a mobile device 108 carried by a carer automatically to attend to a subject $106_n$ being monitored in particular circumstances. These circumstances include, for example, when a risk of wetness leakage calculated by the processor exceeds a threshold risk considered to be acceptable according to a care plan or accepted standard of care. An acceptable threshold risk may be e.g. 50%, 60%, 70% or 80%. The acceptable risk may be different for different subjects. Alternatively, the acceptable risk may be determined according to the "care level" applicable to a subject or group of subjects. Additionally, processor 102 may transmit an alert to a carer's hand-held device 108 when the transmitter T (or processor) establishes that the sensor 200 and the transmitter T are disconnected, or when transmission from the transmitter to processor 102 has ceased. Similarly, an alert may be transmitted when low power remains in a battery powering a transmitter or when processor 102 detects that data collection from a particular transmitter T has ceased. In one embodiment, the transmitter T includes a motion detector generating signals used to determine when the subject has fallen or has potentially fallen; in this scenario processor 102 also sends an alert to the carer's device 108. Processor 102 is configurable to transmit an alert to a carer upon detection of any pre-defined condition detected by sensors coupled to the transmitter T.

In a preferred embodiment, processor 102 is configured to check the integrity of event data provided to the system by a carer. For instance, a carer may indicate that at 2 pm there was a pad change. However, the sensor data shows that at 2 pm there was wetness in the pad, followed by no wetness at 3.30 pm and then a sensor disconnection. This is suggestive of an inaccurate event data entry by the carer since the sensor data indicates that the pad change occurred at around 3.30 pm and not 2 pm. In one embodiment the processor flags the error for correction.

In a preferred embodiment, there are processing means associated with the system is configured to correlate automatically patterns in continence-related data and optionally event data with one or more disease condition indicators and provide automatically guidelines for further investigation to ascertain the possible presence of a disease state. By way of a non-limiting example, a disease state with which the processing means may correlate continence-related data may include one or more of: urinary tract infection, constipation, retention, stress incontinence, nocturia, etc. Table 2 provides an example of continence-related patterns (and event data) and disease conditions which may be associated with those patterns.

The system is configurable to receive inputs from any sensor type that may be used to monitor incontinence in a subject by optimising a mathematical model according to that sensor's behaviour. This is achieved by, during a configuration period, collecting continence-related data for one or more subjects using a sensor of the particular type and also collecting non-wetness event data (time of pad changes and soiled pad weights) for the one or more subjects. At the end of, or during the configuration period which may be e.g. 1, 2, 3 (or more) months or 10, 20, or 30 or more assessments (for establishment of a continence care plan), the event data is used, together with the continence-related data from the sensor, to optimise the mathematical model employed by the volume estimator during monitoring of subjects for incontinence. The optimised model for the particular sensor type is used during actual monitoring and assessment of subjects using sensors of the type for which the processor has been configured. In one embodiment, the optimised model also uses demographic information such as the subject's age, gender and health status (e.g. medications prescribed).

The system may be configured to monitor incontinence in subjects using a range of different sensor types concurrently, where the sensor type can be communicated automatically or manually to processor 102 which then selects an appropriate model to implement for wetness volume estimations and risk of leakage assessments. Automatic communication of sensor type may involve use of a sensor identifier circuit, akin to the pad type identifier circuit described above.

Figure 6A:
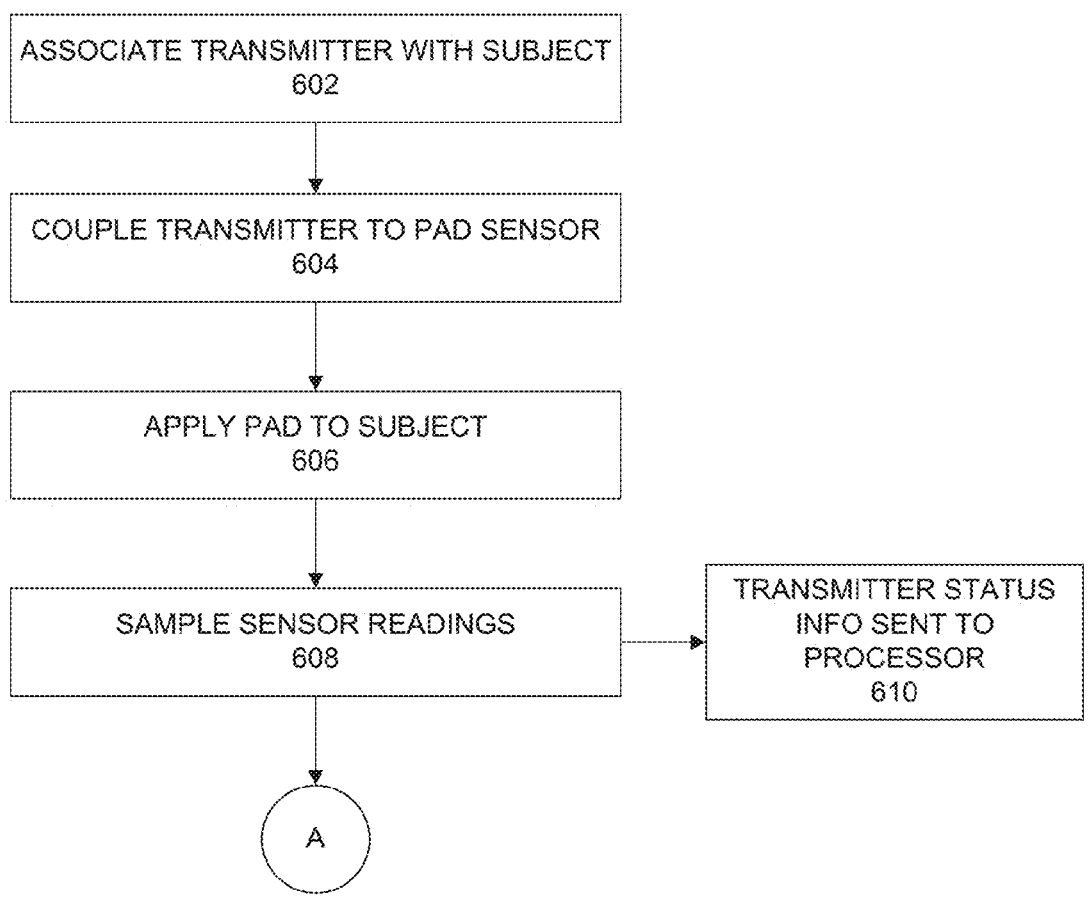
FIGS. 6*a* and 6*b* are flow diagrams representing steps in a method of monitoring continence, according to an embodiment of the invention.
Figure 6B:
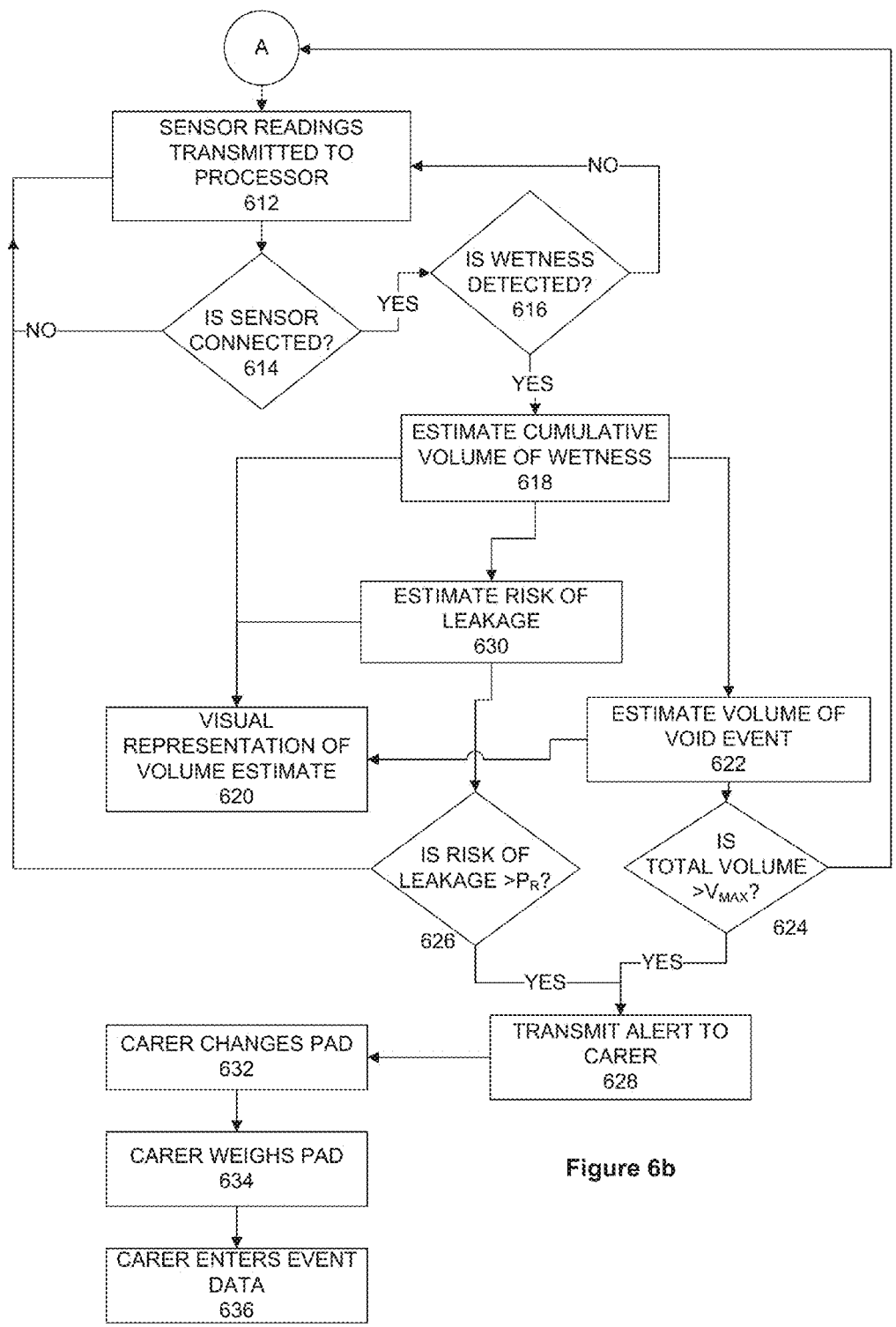

Referring now to FIGS. 6*a* and 6*b*, a flowchart shows steps in a method of monitoring incontinence in a subject using the system. In a step 602 a transmitter T is associated with a subject 106 to be monitored. In a step 604 the transmitter T is coupled to a sensor 200 in a pad 300 and the pad is applied to the subject 106 in a step 606. The transmitter T then samples the sensor values (step 608) while in a step 610 transmitter status information (such as connection strength, battery and network status) are transmitted from transmitter T to processor 102.

Now turning to FIG. 6*b* which continues the method from FIG. 6*a*, in a step 612 the sampled sensor readings are transmitted from the transmitter T to processor 102. Processor 102 simultaneously receives signals from other transmitters being monitored and may use signal multiplexing or other approaches, as would be known to the non-inventive skilled addressee, to receive and process the signals. Processor 102 then ascertains in a step 614 that the sensor is still connected to the transmitter and whether the sensor has detected wetness in the pad (step 616). For a resistive sensor

TABLE 2

| Continence related data | Event data | Disease condition indicator | Guidelines for investigation |
| --- | --- | --- | --- |
| Small voids | frequent | constipation retention UTI | Referral to GP or continence nurse or urologist Bladder scan Stick test with Urine to identify protein, nitrites, leukocytes, bladder or other abnormalities Possible prescription Mid stream urine specimen Check for impaction Abdominal x-ray |
| Void | immediately after manual toileting | retention | Referral to continence nurse Bladder scan |
| Multiple voids | after sleeping/lying flat | Nocturia | Referral to GP or continence nurse Possible prescription of drugs for Nocturia Identifying different positions during toileting Abdominal x-ray |
| Small voids | after movement/reposition | stress incontinence | Referral to GP or continence nurse Bladder scan |
| Large void | When resident stands | Stress incontinence Unstable bladder | Referral to GP or continence nurse | of the type illustrated in FIG. 2, this is achieved by identifying a "leading edge" in the data signal. If no wetness is detected, no action is taken and monitoring continues. If wetness is detected, the volume estimator estimates the cumulative volume of wetness (step 618). In a step 620 a processor causes a visual representation of the volume estimate to appear on the display 103 by plotting the wetness event on the timeline chart (see FIG. 2).

In a step 622 the volume estimator estimates the volume of individual void events which are also presented in the visual representation (step 620). In a step 624, a processor ascertains if the total volume in the pad exceeds a threshold volume, $V_{TH}$. If the total volume exceeds the threshold then in a step 628 the processor transmits an alert to the carer indicating that the subject requires attention. Concurrently, the processor determines a risk of wetness leakage from the pad in step 630. If the risk of leakage does not exceed a pre-defined acceptable risk level then no action is taken and the system continues to monitor continence-related data from the subject. In the event that the risk exceeds the acceptable level, then the processor transmits an alert to the carer in a step 628. Upon receipt of the alert, the carer changes the subject's pad in step 632. The carer may also weigh the soiled pad in a step 634, prior to disposal for input as non-wetness event data which is used in model optimisation. The transmitter is then coupled to a new pad sensor, (step 604) and the method continues. At appropriate times (e.g. at the end of a shift or when time is available, the carer enters non-wetness event data to the system using input means 104. In this scenario the event data includes observation data (e.g. the time of pad change, mass of soiled pad) and other data of relevance such as fluids intake, medication administered, movement observations, changes in the subject's physical condition and the like.

The method of FIGS. 6a and 6b is continued for an assessment period of 3 to 5 days. At the conclusion of the assessment period, the system provides a care plan, in the form of a toileting schedule for the subject, based on correlations between event data and the sensor data identified by the volume estimator executing a mathematical model. The assessment period may be followed by or conclude with an evaluation period of e.g. 1 to 2 days where the subject is cared for according to the care plan but is still monitored using the system to ascertain the accuracy of the care plan as it relates to the subject's usual continence patterns and behaviour and to validate whether toileting the resident at toileting times designated in the care plan reduces number and/or volume of the voids within the absorbent article.

Figure 4:
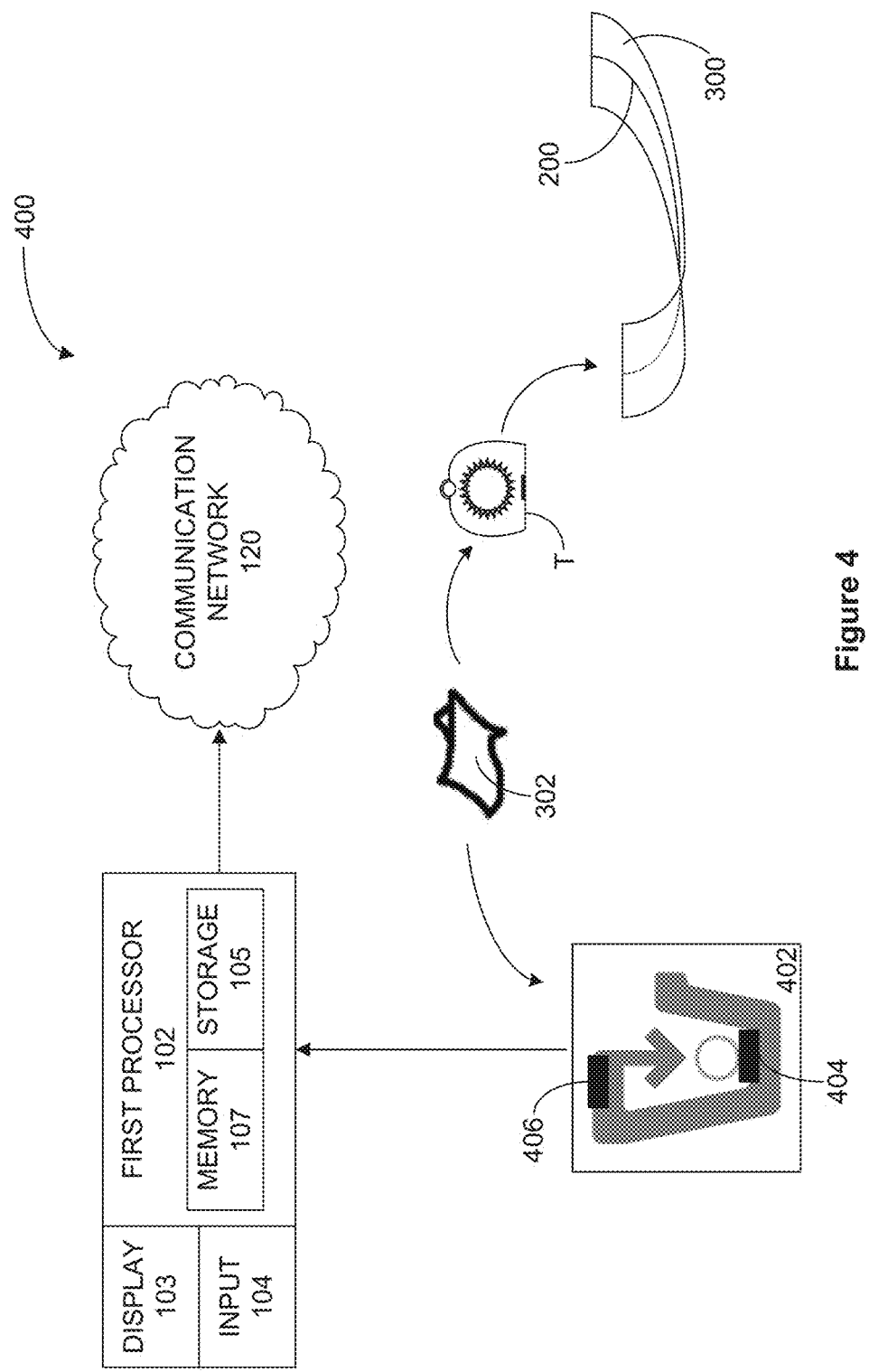
FIG. 4 is a schematic illustration of a system according to an embodiment of the invention intended for use in the home.

In the preceding discussion, the invention has been described in general terms in the context of institutional settings. However, the system, method and sensors may also be used in the home (i.e. residential setting). FIG. 4 is a schematic drawing showing components of a system 400 for use in the home. Processor 102 is in communication with a display 103 and input device 104.

The system includes a waste receptacle 402 fitted with a scale 404. The scale 404 determines automatically the mass of a used pad 302 placed in the waste receptacle 402. Preferably, waste receptacle 402 includes pad type identifying means 406 for identifying the type of pad being disposed of. The pad type identifying means may utilise a pad type indicator circuit on the absorbent article 302 to automatically determine the pad type, as described in the context of institutional use of the system. Alternatively, a scanner may be used, e.g. to scan a barcode on a surface (preferably outer surface) of the absorbent article 302 as it is disposed into the receptacle 402. Alternatively, a contactless device such as a RFID tag may be used to communicate to the processor the pad type, or other identifier circuits as described above. Alternatively the subject or a carer may provide the identity of the pad type manually, using the input means 104 or the system may deduce the pad type on the basis of a disconnection of a particular pad type occurring immediately prior to the disposal of the pad.

The scale 404 and pad type identifying means 406 are in communication, either directly or indirectly via a communication element on the receptacle 402 with the processor 102 to facilitate a determination of the actual voided volume (by calculating the mass difference between the soiled pad 302 prior to disposal, and the mass of the pad 300 when unsoiled). This enables automatic determination of volumes voided in a manner which is accurate and hygienic and only requires minimal cooperation from the subject being assessed. It is contemplated that healthcare services providers would supply individuals being assessed using the in-home version of the system 400 with the waste receptacle 402 for the duration of their assessment, perhaps for a fee. At the conclusion of the assessment or evaluation phase, the receptacle would be returned to the healthcare services provider who will clean it and provide the device to another client for assessment.

In a preferred embodiment processor 102 is also in communication with WAN (wide area network) 120 through which continence-related data and event data may be relayed back to a further processor 150 for offsite monitoring and analysis. Alternatively, the processor 102 may distribute some or all continence-related data and non-wetness event data to multiple further processors for shared monitoring and analysis. Thus, there may be more than one further processor 150. Alternatively, data obtained during home-use may be stored in memory 107 of the processor 102 and downloaded after the system 400 has been returned to the healthcare service provider.

Figure 5:
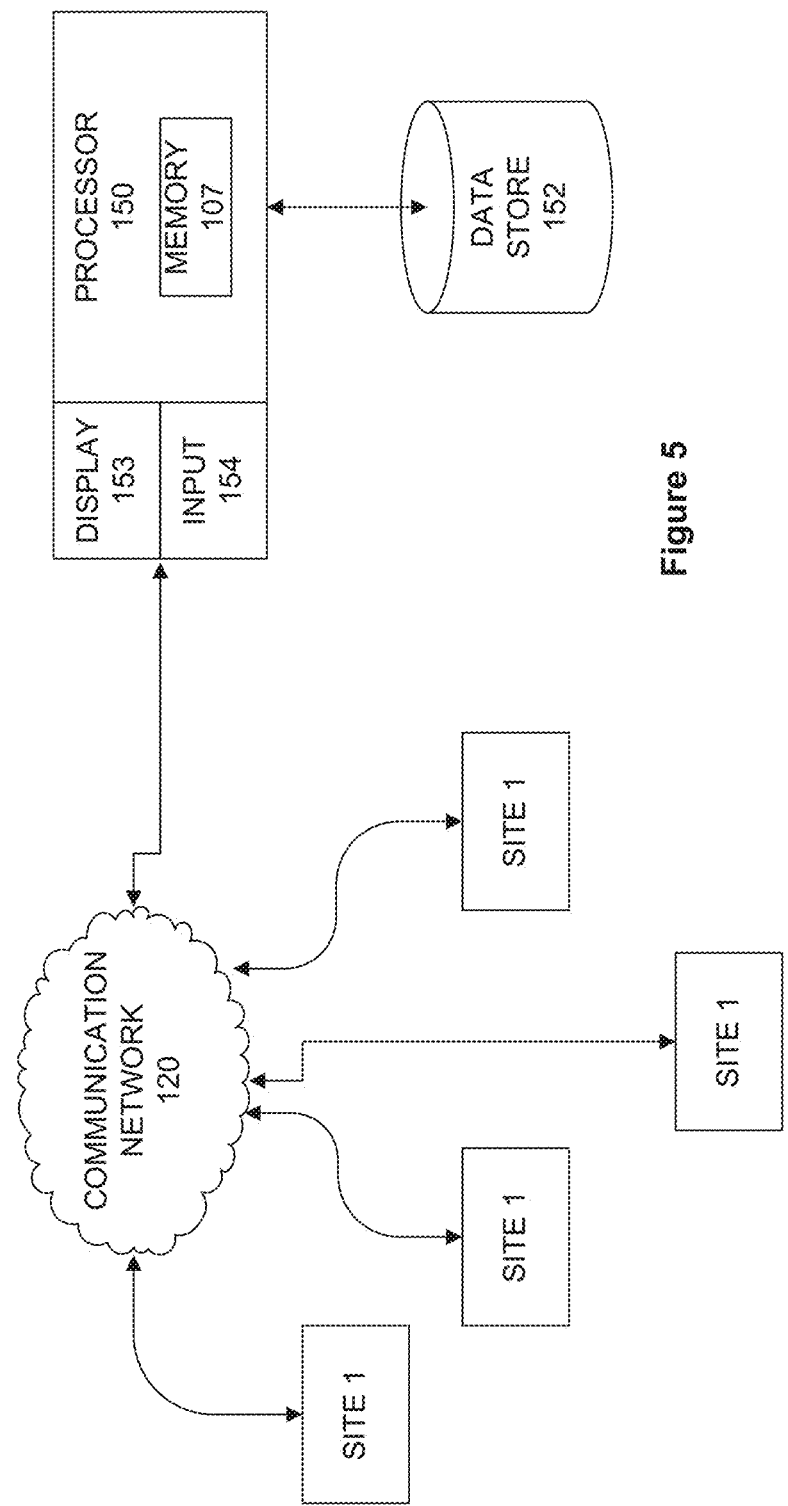
FIG. 5 is a schematic illustration of an embodiment of the invention in which continence-related data from a plurality of sites is communicated to a second processor e.g. for analysis and reporting.

In a preferred embodiment, the systems 100, 400 are configured for multi-site use, as illustrated in FIG. 5. In FIG. 5, sites 1 to 5 each represent an institution or residential (in-home) monitoring system 100 or 400 of the kind illustrated in FIGS. 1 and 4. Processor 150 is a remotely located computing device receiving continence-related data from each of the sites 1 to 5 although it is contemplated that many more sites, in the vicinity of hundreds or thousands of sites, are connectable via network communication elements referred to generally as communication network 120 with processor 150. Processor 150 is in communication with data store 152 storing data received at processor 150 from the multi-sites. Additionally, data store 152 stores the results of analysis performed by processor 150 based on the data obtained from the multi-sites.

Processor 150 may use any remote connection software to facilitate communication with and extraction of data from multi-site processors 102. Additionally, processor 150 is desirably able to view processes running and data stored at the various sites on the respective site processors 102. Data from the multi-site processors may be transmitted in batches using the communication network 120 or in real time. The data may be transmitted in "raw" form or it may be pre-processed at each of the individual sites by respective site processors 102 to reduce the volume of data requiring transmission.

Pre-processing may involve e.g. stripping zero-data (i.e. data collected while the transmitters were not connected to a sensor) from the continence-related data files. Further, dry pad data may be delimited since continuous readings are not required while the pad has been detected as "dry"; the relevant sensor data for analytical purposes pertains to when the pad is applied to a subject and when there has been a wetness event. Technical data which has been used to enhance care during assessment and monitoring but which is not necessary for continence assessment or analysis may also be removed by the site processors 102 prior to compressing the data for transmission, preferably outside peak periods, to the further processor 150. Transmission may be instigated by the processor 102 at each of the individual sites (e.g. a "push" type transmission) or by the further processor 150 (e.g. a "pull" on demand type of transmission) or by a combination of these.

Preferably, the site processors 102 also check the integrity of the data. That is, it checks automatically for concordance between non-wetness event data provided by carers and sensor data obtained from the transmitter. Thus, where non-wetness event data has been entered which conflicts with the sensor data (e.g. non-wetness event data indicating a pad change following a period of sensor data indicating no wetness) this is flagged for correction or removed from the data before transmission to the further processor 150.

The further processor 150 may be utilised in an outsourced assessment model where sensor and event data for a subject are sent to the remote further processor 150 for use in formulating a care plan, production of a bladder diary and the like. For outsourced assessment, the data may be sent continuously in real time or after a delay, or at the conclusion of the assessment period.

Multi-site data is used by further processor 150 to verify and optimise mathematical models executed by one or more volume estimators to estimate void volumes for individual subjects. It is to be understood that the site processors 102 may also verify and optimise mathematical models using data from that site. However more powerful verification and optimisation can be achieved using data from a plurality of sites. Similarly, the multi-site data can be used by the further processor 150 to identify models that are not sufficiently accurate and then optimise them. After optimisation, the further processor 150 communicates optimised models to the respective site processors 102 throughout the network for use in incontinence assessment at the various sites.

The system may utilise data obtained from the multi-sites for a range of purposes and applies statistical and other techniques to identify automatically, correlations between e.g. medications, care techniques, pre-existing and newly arising complaints and conditions, incontinence patterns, pad selection, pad usage and the like.

For instance, the system may be programmable to provide a number of analytical outputs based on extensive data obtained from the plurality of sites to identify trends in usage of absorbent articles/pads. The trends may identify geographical areas where a particular pad type is popular, or demographics where a pad type is more prevalent. This can by used by institutions, governments and even pad manufacturers to adjust ordering and manufacturing volumes, and to efficiently plan and budget for future use.

The system may also utilise event data communicated from the plurality of sites to identify trends in carer behaviour. This can be used by large health care providers, governments and researchers to ascertain whether carers have adequate training, are adhering to standards in healthcare and where standards may be modified to improve patient outcomes, cost effectiveness etc. Multi-site data received by the system may also be used to evaluate general health and care assessment (including continence care plans) for subjects being monitored and may be used to report generally on health care for particular demographics.

In a preferred embodiment, demographic data which may include patient histories and family data may be communicated from the plurality of sites to processing means in the system and used to analyse population data in relation to a range of interesting factors which may be indicative of the prevalence of conditions in populations having certain demographic characteristics. Naturally, patient identifying information is protected or excluded from the data to ensure confidentiality. These factors may include, e.g.: continence, hydration, dementia, wound and pressure care, urinary tract infections, bladder infections, urodynamics, bowel condition, risk of falling or fall frequency and chronic conditions (such as obesity, heart disease, diabetes, asthma and the like) experienced by subjects monitored using the system. These factors may be used to identify correlations between incontinence and other conditions or socio-demographic indicators which can in turn be used to develop or re-develop standards in relation to health care, health care assessment and patient evaluation.

Data obtained by the system may also be utilised to evaluate product performance for pads, sensors and pad/sensor combinations. Thus, the multi-site data may be used to provide benchmark indicators pertaining to the performance of different continence products, and different models of continence care. These indicators may then be used to influence product design, product selection and uptake and different models of continence care.

Generally, it is desirable for the system to collect a range of data which may include, without limitation, demographic data pertaining to subjects monitored at the multi-sites; data pertaining to general health assessment for those subjects, non-wetness event data including manual observations for the subject obtained during monitoring and sensor data collected from the subject. The sensor data includes wetness data but may also include data obtained automatically pertaining to movements of the subject, temperature, urinalysis and the like. Where a physician has used the input device 104 to provide diagnostic or other information relevant to the subject's condition into the system this may also be communicated from the institutional site to the remote processing means, together with data pertaining to changes in the physical and/or mental condition of a subject. Preferably the system also collects care plans (i.e. toileting schedules) from the plurality of sites and where available, details of a subject's medication regime.

These data, once collected are integrated to provide useful reports indicating correlations between various indicators and conditions. The data may be analysed by identifying trends within the data, correlations between the data and prevalence of particular conditions, pad usage trends, carer behaviour, etc in various populations. The analysis can then be used to identify metrics for carer behaviour and trends in carer behaviour. The metrics may include e.g. carer efficiency, response time, effectiveness (or accuracy) of manual observations, effectiveness of interventions with the subject, thoroughness of carers when entering event data and compliance with care standards. These metrics may in turn be used to evaluate workforce training and guide future training requirements Further, the system may utilise data from the plurality of sites to assess the effect of care facility features on the quality and cost of care administered. This may take into account the location of the institution, layout of the area, qualifications of the carers, care protocols implemented, staff to resident ratios, the level and type of care provided and other categorisations in relation to the facility.

The data received by the system may also be analysed to provide indicators of resident wellbeing. Resident well being may be determined by reference to health outcomes, quality of life outcomes, or changes in continence-related data as they are monitored over time. Other indicators of well being may relate e.g. to patient risk profiles such as risk of falling, risk of wandering etc.

The data received by the system may also have utility for providing indicators to pad manufacturers and manufacturers/distributers and purchasers of other consumables used in the system. The data may be analysed to identify and evaluate factors relating to the pads themselves as they are used. These factors may include, without limitation, dynamic performance of the pad as it is worn, comfort indicators, working capacity of the product, absorption performance (e.g. as measured against International standards or manufacturer ratings), leakage performance, the accuracy of the Rothwell method to determine pad capacity and the like. These factors may be used by product manufacturers during supply chain management and to adjust pricing and cost of supply. These can in turn drive product development strategies and be used to identify and develop training requirements for users. Data collected may also be analysed on behalf of institutions for comparison between orders placed and planned usage etc.

Indeed, data from the system may be used in the management of quality initiatives in relation to continence care by enabling carers to check their compliance to statutory/regulatory requirements in force in the context of caring for incontinence sufferers. It also facilitates validation of quality programs (quality assurance) and continuous improvement programs in provision of care and improvement of care protocols. Data from the system can also be relied on as evidence of the provision of appropriate care, and/or identifying areas where increased support and/or training are required.

Importantly, data obtained using the inventive system may also be used to develop skill assessment and competency based training programs which can be implemented and assessed using the system.

The system is configured to monitor subjects for an assessment period and, at the end of the assessment period, provide a care plan or toileting schedule which is used by carers to administer more efficient and effective continence care. Efficiency gains which can be achieved by employing a toileting schedule derived by the system relate to both time saved from reduced manual checking and possible a reduction in the number of pad changes. In addition, because the toileting schedule enables subjects to experience voids by actual toileting, there is less embarrassment involved with pad changes which can lead to improvements in mental wellbeing and quality of life. Preferably, once a toileting schedule has been derived by the system, a period of evaluation follows to ascertain the accuracy of the schedule and revise if necessary.

The system may also be employed in the training of care staff to perform duties required to care for subjects suffering from incontinence. These duties may include e.g. selection of the appropriate type/size of pad for a particular patient, based on the incontinence behaviour of the subject as determined during the assessment period and the level of risk of leakage that a carer is willing (or able, according to standards of care imposed) to accept. The system may also include a training module to train carers in use of the system to monitor incontinence sufferers and evaluate their incontinence condition. The system may also be used to train staff to evaluate the effectiveness of a care plan devised by the system for a particular subject. The system may also be used in staff training to ensure timely attendance to subjects. This aspect of training utilises the automatic alert and event logging functions of the system which can be used to create a report e.g. at the end of a carer's shift, on the appropriateness of the care administered.

It is to be understood that various modifications, additions and/or alterations may be made to the parts previously described without departing from the ambit of the present invention as defined in the claims appended hereto.

Examples of various architectures over which embodiments of the system may be deployed will now be provided.

Figure 10:
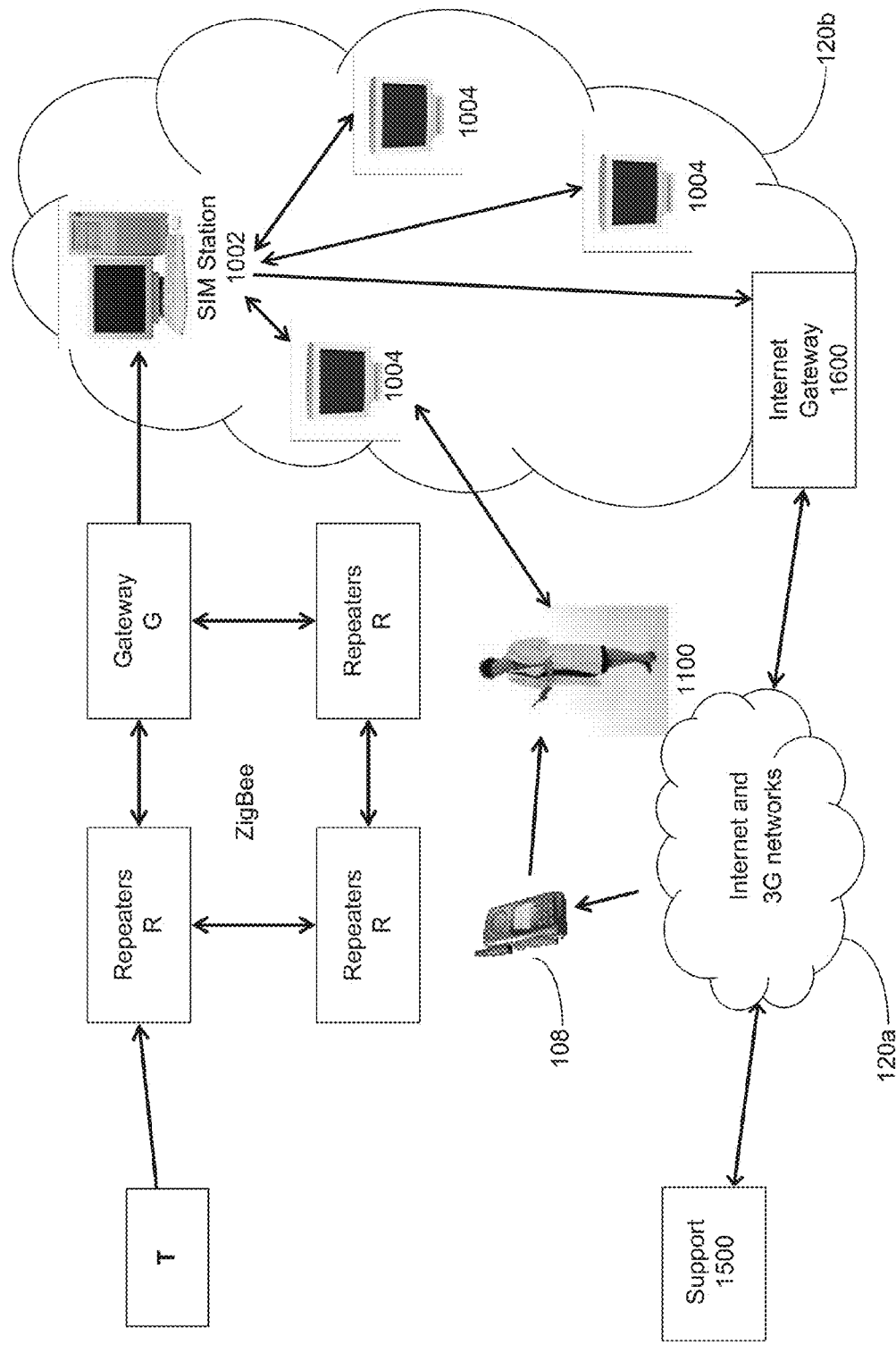
FIG. 10 is a schematic representation illustrating network architecture over which the inventive system may be deployed according to an embodiment of the invention.

FIG. 10 is a schematic representation illustrating one example of hardware architecture over which the inventive system may be deployed. Here, each subject is associated with a device (designated T) having processing capability and which communicates wirelessly with Repeaters R that transmit sensor signals via Gateway G to system processing means located at SIM Station 1002. SIM Station 1002 may further communicate with other processing means 1004 vial local area network (LAN), Wi-Fi or other communication network 120*b*. Processing means 1002, 1004 communicate via an internet gateway 1600 and communication network 120*a* with hand held units 108 held by carers 1100. In the embodiment illustrated, the unit is a phone which may be a generic telephony handset or one which is proprietary to the inventive system. The carer 1100 receives alerts that are transmitted to the hand held unit 108 and may provide input to the system using SIM Station 1002 or input means provided with one of the other processing means 1004. System support 1500 may be provided over the Internet or other communication network 120*a*. This architecture gives considerable control over the platform on which the inventive system is provided. However, it also requires significant outlay for installation of the necessary infrastructure.

Alternatively the hand held unit 108 could be a personal digital assistant (PDA) or smart phone which enables input of data directly by the carer 1100, as well as transmission of alerts from the system to the carer. Carer inputs to the PDA 108 are communicated via wireless internet and 3G communication networks 120*a* to SIM Station 1002 and related processors 1004. A display 103 provided on PDA 108*b* provides a visual representation (e.g. of a chart of the kind illustrated in FIG. 2) of continence related information and this can be viewed at any time by the carer 1100 when carrying the device. Thus, the carer need not return to central SIM Station 1002 to inspect the chart or view the 'risk of wetness' leakage indicator. Further, the facility on PDA for entry of data leads to increased compliance from carers and greater ease of use. This variation may also accommodate applications of the system outside of fixed institutions in individuals homes in the community.

Another variation is where the PDA device 108 is operable with communication network 120*b* but not Internet/3G network communication network cloud 120*a*. Network 120*b* is a LAN provided by Wi-Fi, Ethernet or other local network within the site where the subject is being monitored. This architecture removes reliance on mobile telephone networks, access to which is governed by third parties and which can therefore be costly. Instead, the system operates over networks installed and controlled locally. This model of architecture may provide lower usage data costs.

In another variation, the mobile device 108 is also able to establish direct communications to the transmitter (T) when the caregiver carrying the device is in the vicinity of the resident. This provides the ability to validate that the resident has indeed been attended to. This would replace the more rudimentary functionality of pressing a button or other actuator on the transmitter which causes a time-marked indicator to be transmitted to the processing means which may be used to send the carer a reminder alert for entry of resident observation data.

Figure 11:
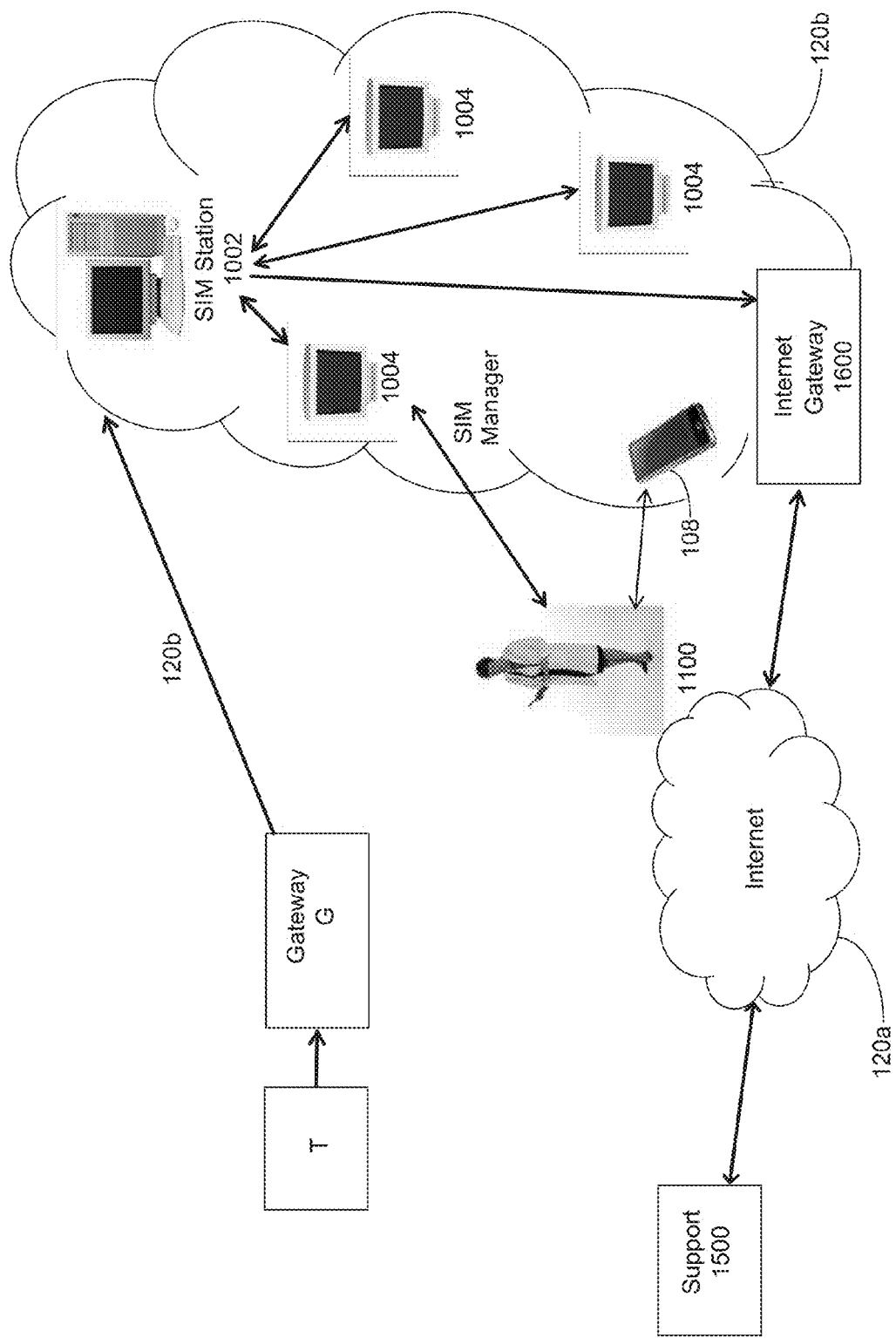
FIG. 11 is a schematic representation illustrating network architecture over which the inventive system may be deployed according to another embodiment of the invention still.

FIG. 11 is a schematic representation illustrating a further variation of the architecture illustrated in FIG. 10. In this arrangement, the Repeaters R are eliminated. Each subject still has a Transmitter T connected to the sensor in the absorbent article, and is also allocated access to a wireless device providing a gateway G for communicating directly with network 120b (a Wi-Fi or Ethernet LAN). Preferably data is acquired from sensors using a low power transmitter T and is conveyed to the processing means (SIM Station 1002 and/or processors 1004) via higher power devices. Gateway G need not be an ambulatory device. Rather, the gateway may be located at the subject's bed side or mounted on a wall with mains power (or other power supply connected). The Gateway may be removed from a charging dock and placed in the subject's pocket or carried by the subject when ambulatory access to the LAN is required. This architecture may be better suited to remote sites where lower complexity infrastructure is desirable.

In another arrangement (not illustrated), the Gateway G is not allocated to the subject (or e.g. to a room in which the subject is resident). Rather, it is built into the hand held unit carried by the subject (not the carer). The hand held unit may be a smart mobile device such as iPad, iPod touch, iPhone or other similar device which is operable on a Wi-Fi or similar LAN. This enables carers 1100 to monitor visual representations on the hand held device, and may also enable subjects to view their own continence-related data and visual representations, and provide inputs to the system (such as food and fluid intake, mobility data, toileting data and the like) on their own device. This arrangement may take advantage of existing Wi-Fi or other LAN infrastructure and accommodates use of generic hardware with the system. Each subject can also be identified automatically. Since the hand held device is allocated to a particular resident, data originating from that device can be automatically associated by the system with that individual. Other embodiments are also contemplated where the subject's hand held device communicates with the SIM Station 1002 and/or other processors 1004 via wireless WAN connections such as the 3G or other networks, although the cost of data transmission over networks owned by third parties may be high. In some embodiments, processing may be performed on the subject's hand held device. For example, the hand held device may contain the mathematical models to calculate volume estimates and risk of wetness leakage during monitoring. In this arrangement, nearly all the processing functionality may be contained within the subject's mobile device, and/or it may communicate with a SIM Station 1002 for review by carers.

In the case where the battery life of the transmitter T could be increased or made more efficient it may also be possible for the transmitter to communicate on existing networks such as the LAN or 3G networks directly, thereby reducing the need to invest in additional infrastructure and simplifying the network topology such that the transmitters T, the hand held units 108 and the SIM station 1002 could all communicate on network infrastructure provided for at a lower cost, more ubiquitously and not exclusively for deployment of the inventive system.

The invention claimed is:

1. A system for monitoring incontinence in one or more subjects, the system comprising:
   a. a display means;
   b. input means operable by a user;
   c. one or more transmitters, each transmitter being associated with one or more subjects being monitored, the one or more transmitters being configured to transmit signals containing continence-related data for the one or more subjects, wherein the continence-related data has been obtained over time from a continence sensor associated with an absorbent article worn by each respective subject;
   d. a receiver unit configured to receive signals from the one or more transmitters; and
   e. processing means in communication with at least the receiver unit, the processing means including a display processor configured to process the received signals and communicate display information to the display means for display of a visual representation of continence-related information derived from continence sensors in the absorbent articles worn by the one or more subjects being monitored;
   wherein the processing means is configured to receive automatically, a sensor status indicator which distinguishes whether a sensor, or absorbent article associated with a sensor, is newly connected to the system or is instead re-connected to the system and wherein the sensor status is determined by reference to a characteristic of a sensor status circuit on the absorbent article and/or the sensor, the characteristic being determined by reference to one or more elements incorporated into the sensor status circuit, said elements selected from a group consisting of capacitors, expirable components, contactless devices, read only memory devices and programmable memory devices; and
   wherein the sensor status circuit is configured to identify automatically a type of sensor and/or the absorbent article with which it is associated, wherein a designated sensor type is associated with a designated value selected from the group consisting of resistance, impedance capacitance, inductance a resonant frequency, carrier frequency and potential difference.

2. The system according to claim 1, wherein the processing means includes a volume estimator configured to apply the continence-related data to a pre-determined mathematical model to estimate a volume of wetness in the absorbent article; wherein the estimated volume of wetness is:
   a. a cumulative wetness volume in the absorbent article; and
   b. a volume of an individual wetness event in the absorbent article.

3. The system according to claim 1, wherein the processing means is configured to receive automatically a pad type indicator for an absorbent article worn by a subject and, based on the pad type indicator and continence-related data collected during wearing of said absorbent article by said subject, calculate a risk of wetness leakage from the absorbent article.

4. The system according to claim 3, wherein the processing means calculates the risk of wetness leakage from the absorbent article using the pad type indicator and a volume estimate determined by the processing means, wherein the risk of wetness leakage calculation is static, or is dynamic and based on continence-related data obtained from the subject over time.

5. The system according to claim 3, wherein the pad type indicator is determined by reference to a characteristic of an identifier circuit associated with the continence sensor, the characteristic being selected from the group including: resistance, impedance, capacitance, inductance, a resonant frequency or a carrier frequency associated with the identifier circuit or a potential difference or current value measurable from the identifier circuit.

6. The system according to claim 5, wherein the identifier circuit is exists in parallel with a sensing circuit associated with the continence sensor.

7. The system according to claim 1, wherein the visual representation shows diagrammatically on a time scale one or more of:
 a. estimated void volumes in the absorbent article of a subject being monitored;
 b. occurrence of one or more non-wetness events specific to the subject being monitored; and
 c. a risk of wetness leakage indicator for an absorbent article worn by a subject being monitored.

8. The system according to claim 1, wherein the one or more transmitters is configured to perform one or more of:
 a. transmitting data to the processing means identifying points in time for which non-wetness event data is required; and
 b. causing a visible and/or audible and/or haptic reminder to be presented to a user, prompting the user to enter the required non-wetness event data using the input means.

9. The system according to claim 8, wherein the input means facilitates manual entry of non-wetness event data by one or more of:
 a. a menu list of items presented on the display means;
 b. one or more actuators on an associated transmitter;
 c. optically, electronically or otherwise scanning a code from a card or other reference guide; and
 d. manual entry of a code;
 wherein any of the foregoing are optionally performed using a hand held device.

10. The system according to claim 1, wherein the processing means is configurable to receive inputs from a particular sensor type by, for a configuration period:
 a. collecting continence data from a sensor of the particular sensor type associated with an absorbent article worn by a subject;
 b. collecting non-wetness event data pertaining to the subject; and
 c. using the collected non-wetness event data and sensor data to optimise a mathematical model executed by the processing means for monitoring incontinence in a subject;
 wherein the optimised model is used to monitor incontinence in a subject wearing an absorbent article with a sensor of the particular sensor type.

11. The system according to claim 1, further including a waste receptacle fitted with a scale, wherein the scale determines a mass of a soiled absorbent article placed in the waste receptacle.

12. The system according to claim 11, wherein the receptacle includes pad type identifying means for identifying a pad type for which the mass is determined by the scale, wherein the pad type identifying means uses one or more of the following to determine pad type:
 a. a pad type indicator circuit associated with a sensor on the absorbent article;
 b. scanning means scanning a barcode on a surface of the absorbent article;
 c. a pad type receiver receiving a pad type signal from a contactless transmitter on the pad;
 d. a sequence of events where disconnection of the pad from the transmitter is followed by deposition of the pad into the receptacle; and
 e. manual entry of a pad type identifier.

13. The system according to claim 1, wherein the processing means includes a data compiling processor receiving multi-site continence-related data obtained from a plurality of sites where the system is used to monitor subjects for incontinence, a data store storing the multi-site data, and one or more network communication elements connecting the one or more sites with the data compiling processor, wherein the data compiling processor utilises data obtained from the plurality of sites to perform automatically, one or more of:
 a. verifying a mathematical model for estimating void volume;
 b. improving a mathematical model for estimating void volume;
 c. identifying trends in usage of absorbent articles;
 d. evaluating care assessments for subjects being monitored;
 e. identifying trends in carer behaviour; and
 f. analysing population data.

14. The system according to claim 1, including one or more sensors for detecting wetness events in an absorbent article, each sensor including an identifier circuit for automatic identification of one or both of a pad type associated with the absorbent article; and a sensor status.

15. The sensor for monitoring continence according to claim 14, wherein the identifier circuit is exists in parallel with a sensing circuit.

16. A method for monitoring incontinence in a subject wearing an absorbent article containing a wetness sensor coupled to a transmitter, the method including the steps of:
 a. transmitting from the transmitter continence-related data to a processor;
 b. estimating a volume of wetness in the absorbent article;
 c. the processor communicating display information to a display means for display of a visual representation of estimated wetness volume with respect to time; and
 d. calculating a risk of wetness leakage for the absorbent article by analysing information selected from the group consisting of the estimate of volume of wetness in the absorbent article, the pad type of the absorbent article and/or the pad type of the wetness sensor.

17. The method according to claim 16, including the step of operating an input means to provide to the processor time-marked non-wetness event data and causing the processor to include on the visual representation the time location of one or more non-wetness events for a subject being monitored.

18. The method according to claim 16, including the step of providing a visual representation on the display means which is indicative of the calculated risk of wetness leakage.

19. The method according to claim 16, including determining automatically when the risk of wetness leakage exceeds a pre-determined acceptable risk and transmitting automatically an alert to a carer for the subject being monitored.

20. The method according to claim 16, including determining automatically when the estimated volume of wetness in an absorbent article exceeds a pre-determined threshold volume and transmitting automatically, an alert to a carer for the subject being monitored.

21. The method according to claim 16, further including the step of transferring continence-related data to an analysis processor receiving continence-related data from a multiplicity of sites and collating, packaging, extracting, correlating, integrating and/or analysing the multi-site data for use by an entity selected from a group including: hospitals, care institutions, manufacturers of absorbent articles, governments, health insurers, researchers.

* * * * *